(12) United States Patent
Brummett et al.

(10) Patent No.: US 12,109,424 B2
(45) Date of Patent: Oct. 8, 2024

(54) MEDICAL DEVICE BATTERY RETENTION AND EJECTION ELEMENT

(71) Applicant: Physio-Control, Inc., Redmond, WA (US)

(72) Inventors: Jeremy Edward Brummett, Redmond, WA (US); Neal Stanley Clark, Snohomish, WA (US); Steven Chester, Kirkland, WA (US); Ethan Boehm, Bothell, WA (US); Kathy Wang, Bellevue, WA (US); Alexander Hamilton, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 903 days.

(21) Appl. No.: 17/162,876

(22) Filed: Jan. 29, 2021

(65) Prior Publication Data

US 2021/0236834 A1   Aug. 5, 2021

Related U.S. Application Data

(60) Provisional application No. 62/968,741, filed on Jan. 31, 2020.

(51) Int. Cl.
*A61N 1/39* (2006.01)
*B21D 5/00* (2006.01)
(Continued)

(52) U.S. Cl.
CPC ......... *A61N 1/3968* (2013.01); *A61N 1/3904* (2017.08); *A61N 1/3975* (2013.01); *B21D 5/00* (2013.01); *B21D 28/26* (2013.01); *H01M 50/244* (2021.01); *H01M 50/247* (2021.01); *H01M 50/262* (2021.01); *H01M 2220/30* (2013.01)

(58) Field of Classification Search
CPC ............. H01M 50/247; H01M 50/262; H01M 50/244; A61N 1/39; A61N 1/3968; A61N 1/3904; A61N 1/3975; B21D 5/00; B21D 28/26

See application file for complete search history.

(56) References Cited

U.S. PATENT DOCUMENTS 6,511,770 B2 * 1/2003 Chang ................. H01M 50/209
429/96
RE40,681 E 3/2009 Pitzen et al.
(Continued)

*Primary Examiner* — Karie O'Neill Apicella
(74) *Attorney, Agent, or Firm* — Lee & Hayes, P.C.

(57) ABSTRACT

Systems to retain a battery within, and to eject a battery from, a battery receptacle of a medical device, such as a portable defibrillator, are described. A battery receptacle of a medical device includes an element that is configured to engage an inserted battery to prevent, or reduce, movement of the battery within the receptacle and to assist with removing the battery from the receptacle. In an example, the element is a monolithic structure that includes a retention portion and an ejection portion. The retention portion is positioned at a side wall of the battery receptacle, and the ejection portion terminates in a free end positioned a distance from the side wall. When the battery is inserted into the battery receptacle, the retention portion exerts a retention force on a side surface of the battery, and the ejection portion exerts an ejection force on an end surface of the battery.

20 Claims, 11 Drawing Sheets

(51) Int. Cl.
*B21D 28/26* (2006.01)
*H01M 50/244* (2021.01)
*H01M 50/247* (2021.01)
*H01M 50/262* (2021.01)

(56) References Cited

U.S. PATENT DOCUMENTS

| | | |
|---|---|---|
| 9,263,716 B2 | 2/2016 | Szoke et al. |
| 2011/0022032 A1 | 1/2011 | Zemlok et al. |
| 2016/0166250 A1 | 6/2016 | Marczyk |
| 2017/0042535 A1 | 2/2017 | Racenet et al. |
| 2017/0245854 A1 | 8/2017 | Zemlok et al. |
| 2017/0258467 A1 | 9/2017 | Williams et al. |
| 2017/0311938 A1 | 11/2017 | Nicholas et al. |
| 2018/0340806 A1 | 11/2018 | Zemlok |
| 2019/0046181 A1 | 2/2019 | McCuen |
| 2019/0076135 A1 | 3/2019 | Ross et al. |
| 2020/0262368 A1* | 8/2020 | Lunde .................... H01R 12/53 |

* cited by examiner

MEDICAL DEVICE BATTERY RETENTION AND EJECTION ELEMENT

CROSS-REFERENCE TO RELATED APPLICATION

This application claims the benefit of U.S. Provisional Application No. 62/968,741, titled "Medical Device Battery Retention and Ejection Element" and filed on Jan. 31, 2020, which is incorporated by reference herein in its entirety.

BACKGROUND

Portable medical devices, such as defibrillators, are life-saving tools that are transported to a patient to provide patient monitoring and treatment, and are moved with a patient along the chain of care. These medical devices are configured to be powered by portable power sources, such as batteries. Energy held by a battery depletes over time, and when the energy is depleted, the battery needs to be replaced. Removing and replacing the batteries of a medical device is often a difficult or time-consuming process. For example, batteries are sometimes contained within a compartment of the medical device that is covered and locked, making it difficult or time-consuming to access the interior of the compartment to replace the batteries. While the batteries are being replaced, the medical device cannot be used, which delays patient treatment and monitoring for the duration of the downtime. In some medical devices, the batteries are affixed to the exterior of the medical device, but these externally-affixed batteries are prone to being dislodged or disconnected inadvertently, which also delays patient treatment or monitoring.

Additionally, batteries sometimes move within the compartment, which can cause the battery to disengage from the electrical contacts within the battery receptacle, thereby interrupting an electrical connection between the batteries and the electronic components of the medical device. This interrupted electrical connection causes power disruption that delays patient treatment and monitoring using the medical device. Further, the movement of the batteries within the compartment can damage the electrical contacts in the compartment or on the batteries themselves. The movement can also cause unwanted noise that may distract users of the medical device. The disclosure made herein is presented with respect to these and other considerations.

DETAILED DESCRIPTION

Figure 1:
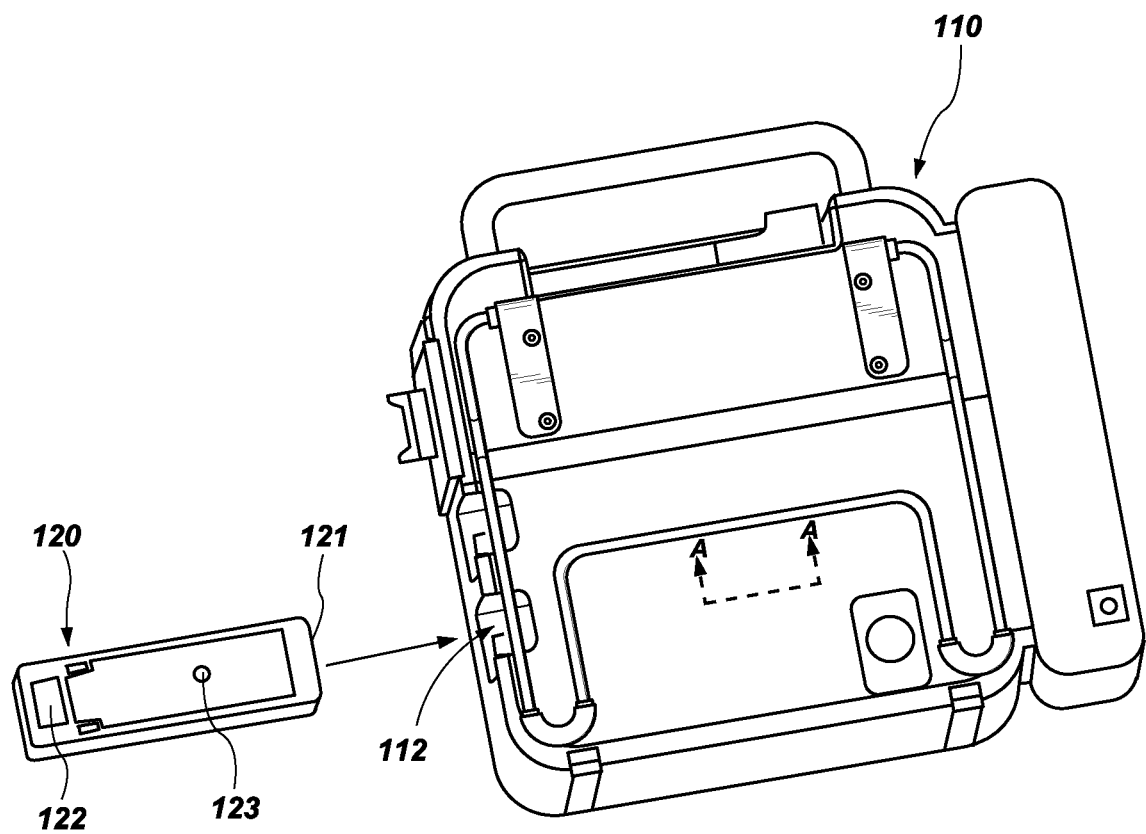
FIG. 1 illustrates examples of a battery and a medical device.

Batteries and other types of power sources are used to power medical devices, such as defibrillators, so that the medical device does not have to be tethered to a fixed power source, like a power outlet. The portable nature of some of these medical devices allows them to be transported to a patient in a variety of situations and environments, such as a patient experiencing a cardiac event. It is this portability that allows patients to receive prompt, life-saving medical attention at the site of a medical emergency. Delays and inefficiencies associated with the battery, such as delays that occur while replacing the battery, hinder the use of the medical device. Furthermore, movement of the battery within the medical device also hinders the use of the medical device, decreases the lifespan of the battery, and damages the electrical contacts on the battery, on the medical device, or on both, which increases the frequency of maintenance for the battery and the medical device.

The disclosure provides apparatuses to efficiently remove one or more batteries from a battery receptacle(s) of a battery-powered medical device, and to retain the battery (ies) within the battery receptacle(s) of the medical device. A battery receptacle of the medical device is configured to receive a battery to provide power to the medical device. According to some examples, the battery receptacle is a cavity that includes one or more electrical contacts at or near a closed end of the battery receptacle that is opposite an open end of the battery receptacle through which the battery is inserted into the battery receptacle. When the battery is inserted into the battery receptacle of the medical device, electrical contacts of the battery engage electrical contacts of the battery receptacle to form an electrical connection between the battery and the medical device (e.g., electronic components of the medical device) and to transfer energy stored chemically in the battery to the electronic components of the medical device to power the electronic components.

Various implementations described herein relate to a battery retention and ejection element that is configured to be disposed within a battery receptacle, systems that include the battery retention and ejection element, and processes involving the battery retention and ejection element, such as processes for forming the element. According to some examples, the disclosed battery retention and ejection element is a single-part element (e.g., a monolithic structure) that is positioned within a battery receptacle of the medical device, such as mounted to one or more surfaces of the battery receptacle. Upon insertion of a battery into the battery receptacle, the battery comes into contact with the battery retention and ejection element within the battery receptacle. When the battery presses the battery retention and ejection element, the battery retention and ejection element exerts a retention force on the battery to prevent, or reduce, movement of the battery within the battery receptacle, and the battery retention and ejection element also (e.g., contemporaneously) exerts an ejection force on the battery to assist with removal of the battery from the battery receptacle. This helps to retain the battery within the battery receptacle when the battery is to remain within the receptacle, and to eject the battery from the battery receptacle when a user wishes to remove the battery. As used herein, the term "battery" means any portable power source capable of powering an electronic device, such as a medical device, and the term "battery" includes both rechargeable power sources and single-use power sources. Here, battery is discussed as a single battery although it can also include multiple batteries. This reference to "battery" generally means the component that provides power to the medical device without regard to the type of power or the configuration of the battery.

In an example configuration, the battery retention and ejection element is a one-piece leaf spring that includes a mounting portion, a retention portion, a bent portion, and an ejection portion. The mounting portion of the battery retention and ejection element is configured to couple (e.g., mount) the battery retention and ejection element to a surface (e.g., a surface of a mounting element) within the battery receptacle. Since the mounting portion is mounted to a surface within the battery receptacle, the mounting portion is prevented from moving within (e.g., relative to) the battery receptacle.

According to some examples, the bent portion of the battery retention and ejection element is curved and is interposed between the retention portion and the ejection portion of the battery retention and ejection element. According to some examples, the retention portion and the ejection portion are substantially planar. According to other examples, one or both of the retention and ejection portions include a slight curvature. The bent portion orients the ejection portion at an angle relative to retention portion, thereby causing the ejection portion to be inclined relative to the retention portion. In an example, an acute angle is formed between the retention portion and the ejection portion due to the relative orientations of the retention portion and the ejection portion caused by the bent portion. According to some examples, the retention portion is interposed between the mounting portion and the bent portion, and the retention portion is positioned substantially flat against a side wall of the battery receptacle and next to the mounting portion. The inclination of the ejection portion causes the ejection portion to extend from the side wall of the battery receptacle into the cavity of the battery receptacle. The ejection portion terminates in a free end that is positioned a distance from the side wall and is moveable. In some examples, the retention portion and the ejection portion are each configured to flex and deflect in response to a force applied to the free end of the ejection portion, such as when the battery is inserted into the battery receptacle and comes into contact with the free end to cause the retention and ejection portions to flex and deflect.

According to some examples, the battery retention and ejection element is in an initial state prior to insertion of a battery within the battery receptacle. As the battery is inserted into the battery receptacle, the battery comes into contact with and exerts a force on the free end of the ejection portion, causing the free end of the ejection portion to be displaced from an initial position. The displacement of the free end of the ejection portion causes the ejection portion to deflect from an initial position, thereby storing potential energy within the battery retention and ejection element. According to some examples, the deflection of the ejection portion causes a deflection of the retention portion of the battery retention and ejection element from an initial position. The retention portion and the ejection portion are each biased to return to the initial position upon removal of the battery from the battery receptacle because of the material properties of the battery retention and ejection element. As such, portions of the battery retention and ejection element create a potential energy that is stored when the portions of the battery retention and ejection element are deflected, and the stored potential energy is released when the deflected portions cease to be deflected, returning to their initial positions under a biasing force. This allows the battery retention and ejection element to exert forces onto the battery. The exerted forces include the retention force exerted on the battery by the retention portion, and the ejection force exerted on the battery by the ejection portion. The retention force prevents, or reduces, movement of the battery within the battery receptacle, and the ejection force assists with removing the battery from the battery receptacle.

The retention portion of the battery retention and ejection element is configured to contact, and to exert the retention force on, a first (e.g., side) surface of the battery while the battery is disposed within the battery receptacle of the medical device. According to some examples, the retention portion of the battery retention and ejection element is configured to deflect away from the side wall of the battery receptacle and towards the battery when a portion (e.g., the ejection portion) of the battery retention and ejection element is pressed by the inserted battery. The deflection of the retention portion causes the retention portion to bow toward the battery and to contact the first (e.g., side) surface battery to exert the retention force on the battery. In an example, the retention force is oriented at an angle relative to the side surface of the battery to compress and clamp the battery against an interior side surface of the battery receptacle that is opposite the surface of the battery receptacle on which the retention portion of the battery retention and ejection element is positioned. In an example, the retention force is oriented substantially orthogonal to the side surface of the battery. According to some examples, the retention force is oriented at an angle less than or greater than 90 degrees relative to the side surface of the inserted battery.

The ejection portion of the battery retention and ejection element is configured to contact, and to exert the ejection force on, a second (e.g., end) surface of the battery while the battery is disposed within the battery receptacle of the medical device. According to some examples, the ejection portion of the battery retention and ejection element is configured to exert the ejection force on another side surface of the battery that is a different side surface than the side surface against which the retention force is exerted by the retention component. The ejection force is exerted in a second direction that is counter to a direction in which the battery is inserted within the battery receptacle. That is, the ejection force is aligned with, or includes a component that is aligned with, and is opposite to, the direction in which the battery is inserted into the battery receptacle. In this manner, the ejection force exerted on the battery is oriented to eject the battery from the battery receptacle.

FIG. 1 illustrates an example battery 120 and a medical device 110. According to some examples, the medical device 110 is a portable medical device, such as a portable defibrillator (e.g., an external defibrillator), that includes on one or more batteries 120 that are configured to provide electrical power for function(s) or feature(s) of the medical device 110. In an example, the medical device 120 is a monitor-defibrillator. The portable nature of the medical device 110 allows the medical device 110 to be used in a variety of situations, such as being brought to a patient in distress and transported with the patient to support the patient's care during transport of the patient to, and upon arrival at, a medical facility, such as a hospital. In another example, the medical device 110 is an in-hospital, portable or non-portable (e.g., situated) medical device 110 that uses a connection to an external power source to provide electrical power for one or more functions and features of the medical device 110. These in-hospital medical devices 110 often include internal batteries as a back-up power source in case the external power connection is unavailable or intermittent, or to briefly move the medical device 110 from one power outlet to another power outlet without disrupting treatment. A battery retention and ejection element is included in a battery receptacle 112 of the medical device 110 to prevent, or reduce, motion of the battery 120 while the battery 120 is disposed within the battery receptacle 112, and to help remove the battery 120 from the battery receptacle 112.

In the example of FIG. 1, the medical device 110 includes one or more battery receptacles 112 for receiving the battery 120. The battery 120 includes electrical contacts (e.g., a connector including electrical contacts) on an end surface 121 (sometimes referred to herein as a "rear end" or a "rear end surface") of the battery 120. When the battery 120 is inserted into the battery receptacle 112, the electrical contacts of the battery 120 come into contact with electrical contacts (e.g., a connector including electrical contacts) within the battery receptacle 112 of the medical device 110. The contact established between these respective electrical contacts form an electrical connection between the battery 120 and the medical device 110 (e.g., electronic components of the medical device 110). The electrical connection between the battery 120 and the medical device 110 allows for the transfer of electrical energy between the battery 120 and the medical device 110 to provide electrical power to the electrical components that facilitate various patient monitoring and treatment capabilities of the medical device 110.

According to some examples, in order to secure the battery 120 within the battery receptacle 112, the battery 120, the medical device 110 (e.g., the battery receptacle 112), or a combination thereof includes a locking mechanism. According to some examples, the locking mechanism is configured to lock automatically, such as upon fully inserting the battery 120 into the battery receptacle 112. In an example, the locking mechanism is configured to be actuated after the battery 120 has been fully inserted into the battery receptacle 112 to unlock the locking mechanism. In some examples, a user unlocks the locking mechanism, or a portion thereof, to allow the battery 120 to be removed from the battery receptacle 112. In this manner, the locking mechanism prevents unintentional removal of the battery 120 from the battery receptacle 112. In the example of FIG. 1, the battery 120 includes a push button 122 (sometimes referred to herein as a "tab") that is configured to be actuated by a user to unlock a locking mechanism and to allow the battery 120 to be removed from the battery receptacle 112. In this example, the user depresses the push button 122 to unlock the locking mechanism to remove the battery 120 from the battery receptacle 112. To help remove the battery 120 from the battery receptacle 112, the battery retention and ejection element exerts an ejection force on the battery 120 to eject at least a portion of the battery 120 from the battery receptacle 112. When the user actuates the push button 122 to unlock the locking mechanism, the battery 120 is no longer secured within the battery receptacle 112, and the ejection force of the battery retention and ejection element causes the ejection of at least a portion of the battery 120 from the battery receptacle 112. In this manner, the user does not have to spend time trying to extract or remove the battery 120 from the battery receptacle 112 and instead grasps the ejected portion of the battery 120 to quickly and easily remove the battery 120 from the battery receptacle 112. According to some examples, the open end of the battery receptacle 112 includes a door to enclose the battery 120 within the battery receptacle 112.

Figure 2A:
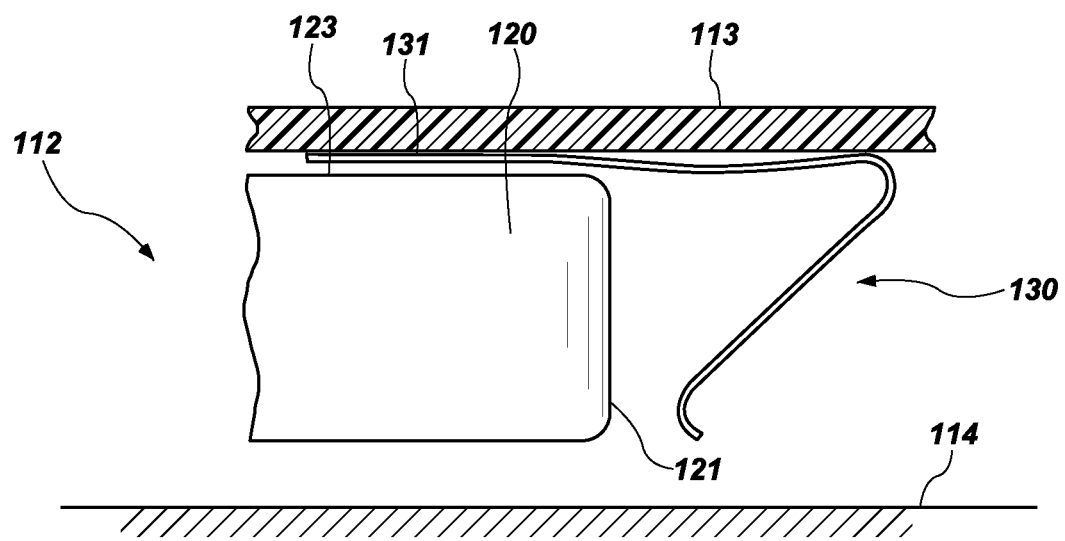
FIG. 2A illustrates a cross-section view of a portion of an example battery receptacle having an example battery retention and ejection element disengaged from a battery.
Figure 2B:
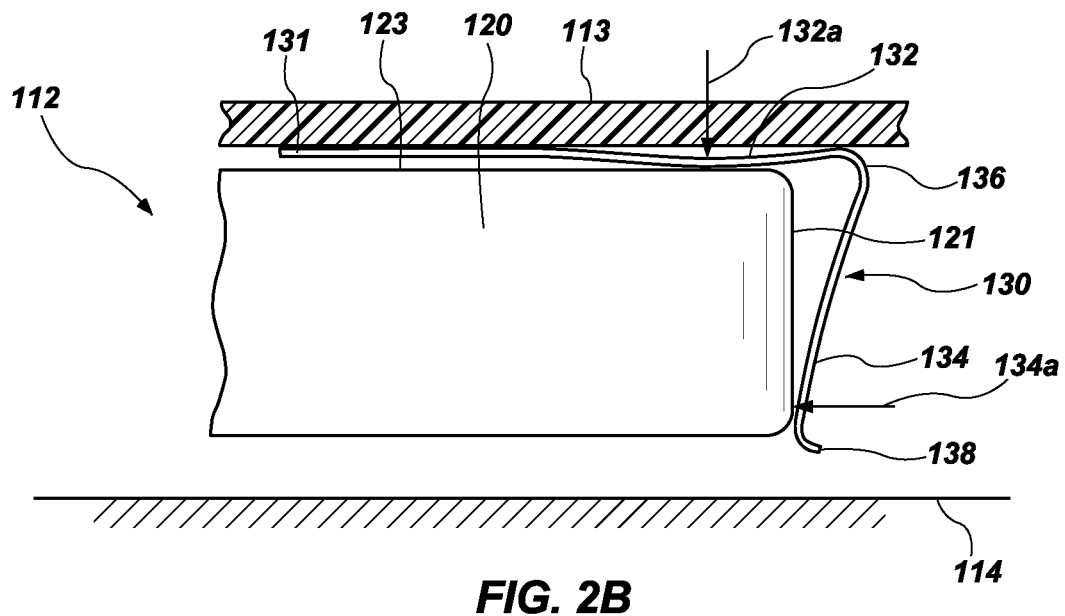
FIG. 2B illustrates a cross-section view of the portion of the example battery receptacle and element depicted in FIG. 2A, the element being engaged with the battery in FIG. 2B.

FIGS. 2A and 2B illustrate a cross-section view of the battery receptacle 112, taken along section line A-A shown in FIG. 1. FIGS. 2A and 2B respectively show the battery 120 at two different times in the process of inserting the battery 120 into the battery receptacle 112 and engaging with a battery retention and ejection element 130 (sometimes referred to herein as an "element" or a "spring"). FIG. 2A illustrates a cross-section view of a portion of an example battery receptacle 112 having an example battery retention and ejection element 130 disengaged from a battery 120. FIG. 2B illustrates a cross-section of the portion of the example battery receptacle 112 and the example battery retention and ejection element 130 of FIG. 2A, the element 130 engaged with the battery 120 in FIG. 2B. In the example of FIGS. 2A and 2B, the element 130 is positioned within the battery receptacle 112 and mounted to a back plate 113 that is removably coupled to an interior, side surface of the battery receptacle 112. The battery receptacle 112 has one or more side surfaces that surround the side surface(s), such as side surface 123, of the battery 120. A battery receptacle 112 with a cylindrical cavity has a single, continuous side wall. A battery receptacle 112 with a rectangular cuboid cavity has multiple side walls. According to some examples, the back plate 113 is removably coupled to a portion of a housing of the medical device 110 to enclose a portion of the battery receptacle 112. In an alternative example, the battery retention and ejection element 130 is mounted to another surface of the battery receptacle 112, such as surface 114 (e.g., another side surface 114).

In FIG. 2A, the battery 120 is not engaged by the battery retention and ejection element 130, such as when the battery 120 is in the process of being inserted into, or removed from, the battery receptacle 112. Since the element 130 is disengaged from the battery 120 in FIG. 2A, the element 130 is in an initial state (sometimes referred to herein as a "relaxed state"). In the initial state of the element 130, the portions of the element 130 are each in a respective initial position. In FIG. 2B, the battery 120 is engaged with the element 130, such as when the battery 120 is fully inserted into the battery receptacle 112. When the battery 120 is engaged with the element 130, the battery 120 presses upon the element 130, portions of the element 130 deflect from their respective initial positions, and the element 130 exerts both a retention force 132a and an ejection force 134a on the battery 120. The retention force 132a compresses and clamps the battery 120 against the side surface 114 of the battery receptacle 112, such as the side surface 114 opposite the side surface (e.g., back plate 113) to which the element 130 is mounted. In an example, the battery 120 includes electrical contacts (e.g., a connector including electrical contacts) at or near the end surface 121 of the battery 120 that are configured to couple to electrical contacts (e.g., a connector including electrical contacts) within the battery receptacle 112 to electrically connect the battery 120 and the medical device 110 (e.g., electronic components of the medical device 110).

According to some examples, the battery retention and ejection element 130 includes a mounting portion 131, a retention portion 132, an ejection portion 134, and a bent portion 136. In the example of FIGS. 2A and 2B, the retention portion 132 has a curvature to assist with the deflection of the retention portion 132 in a direction away from the side wall of the battery receptacle 120 and towards the inserted battery 120. As the battery 120 is inserted into the battery receptacle 112, the battery 120 comes into contact with a free end 138 of the ejection portion 134 of the element 130 positioned a distance from the side wall of the battery receptacle 112 at or near the closed end of the battery receptacle 112. In an example, the battery 120 contacts the free end 138 of the ejection portion 134 (sometimes referred to herein as the free end 138 of the element 130) that is suspended within the cavity of the receptacle 112 and in the path traveled by the battery 120 when the battery 120 is inserted into the receptacle 112). When the battery 120 presses upon the free end 138, the free end 138 is displaced from an initial position shown in FIG. 2A to a displaced position shown in FIG. 2B. This displacement of the free end 138 causes the ejection portion 134 to deflect and a force to be applied to the bent portion 136 of the element 130. The back plate 113 and the coupled mounting portion 131 restrain the element 130 from translating within the battery receptacle 112. Accordingly, the force applied by the battery 120 to the ejection portion 134 at the free end 138 causes the bent portion 136 to rotate. The rotation of the bent portion 136 causes the element 130 to store potential (e.g., "spring") energy and causes the retention portion 132 to deflect and exert the retention force 132a on the battery 120, such as on a side surface 123 of the battery 120. As the battery 120 is inserted further within the battery receptacle 112, the battery 120 continues to displace the free end 138 of the element 130 until the battery 120 is seated within the battery receptacle 112 and the element 130 is deflected to its maximum position. The maximum deflected position of the element 130 occurs when the battery 120 is completely inserted into the battery receptacle 112. The exerted retention force 132a on the battery 120 by the element 130 retains the battery 120 within the battery receptacle 112 and prevents, or reduces, movement of the battery 120 transversely between the back plate 113 and the side surface 114 of the battery receptacle 112. In some examples, the retention force 132a prevents movement of the battery 120 along the length of the battery receptacle 112, such as towards or away from the open end of the battery receptacle 112. This is due to the retention force 132a clamping the battery 120 and causing frictional force(s) that is not overcome by gravity, and is not easily overcome by other forces on the battery 120 due to the movement of the medical device 110, such as when the medical device 110 is jostled or bumped during transport. Similarly, side-to-side movement (into and out of the page for the views shown in FIGS. 2A and 2B) within the battery receptacle 112 is prevented, or reduced, due to the frictional forces caused by the retention force 132a exerted on the battery 120. By preventing the battery 120 from moving within the battery receptacle 112, disruption of the electrical connection between the battery 120 and the medical device 110 (e.g., electronic components of the medical device) and potential noise caused by the battery 120 contacting the walls of the battery receptacle 112 is reduced, if not prevented. According to some examples, the battery receptacle 112 is a shape that is complementary to the battery 120 (e.g., a shape that is conformed to, and fits closely around, the shape of the battery 120) to further reduce the movement of the battery 120 within the battery receptacle 112, such as when the medical device 110 moves during arrival at an emergency site to reach a patient, or during patient transport after the patient is deemed to be in a medical condition suitable for transport to a medical facility, like a hospital.

The element 130, when deflected by the battery 120, is biased to return to an initial state, such as due to the material properties of the element. In other words, the retention portion 132 and the ejection portion 134 are each configured to deflect from an initial position when the battery 120 is inserted into the battery receptacle 112, and biased to return to the initial position when the battery 120 is removed from the battery receptacle 112. The force applied by the battery 120 onto the element 130 causes the element 130 to be displaced from this initial state and to store potential energy. In this manner, when the battery 120 is disposed within the battery receptacle 112, the ejection portion 134 of the element 130 exerts the ejection force 134a (due to stored potential energy) on the end surface 121 of the battery 120. The stored potential energy of the element 130 is released when the battery 120 is removed from the battery receptacle 112, such as when a locking mechanism securing the battery 120 in the receptacle 112 is unlocked. In an example, a user depresses the push button 122 on the battery 120 to unlock the locking mechanism. When the battery 120 is unsecured and allowed to be withdrawn from the battery receptacle 112, the bent portion 136 biases back to its original shape and position, which causes the free end 138 of the ejection portion 134 to also return to its initial state. The release of the potential energy and movement of the free end 138 exerts the ejection force 134a on the battery 120 by the ejection portion 134, which causes the battery 120 to be pushed out of the battery receptacle 112, towards the open end of the receptacle 112. Upon withdrawal of the battery 120 from the battery receptacle 112, the element 130 releases its stored potential energy and returns to its initial state. As the element 130 returns to the initial state, the retention portion 132 also ceases contact with the side surface 123 of the battery 120 so that the retention force 132a is no longer applied to the side surface 123 of the battery 120.

In FIG. 2B, the ejection force 134a is exerted on battery 120 by the contact of the free end 138 with the end surface 121 of the battery 120 since the element 130 is biased to return to the initial state. The ejection force 134a, or a component thereof, is aligned longitudinally with the battery 120 to cause the battery 120 to move out of the battery receptacle 112. Such motion of the battery 120 is prevented due to the locking mechanism that secures the battery 120 within the battery receptacle 112. Once the locking mechanism is unlocked, there is no longer a force countering the ejection force 134a and the battery 120 is ejected from the battery receptacle 112. The ejection force 134a causes the battery 120 to move out of the battery receptacle 112 so that at least a portion of the battery 120 protrudes from the battery receptacle 112, which assists a user with removing the battery 120 from the battery receptacle 112 because the user can grab the protruding portion of the battery 120 with his/her fingers. Additionally, as the element 130 returns to its initial state (e.g., rest position) the exerted retention force 132a on the battery 120 is similarly lessened, or eliminated, which further helps withdraw the battery 120 from the battery receptacle 112.

As shown in the example of FIG. 2A, the retention portion 132 has a curvature (e.g., a slight curvature or bend to the otherwise planar shape of the retention portion 132). The retention portion 132 is generally aligned with a mounting portion 131 of the element 130 in the example of FIG. 2A. As the battery 120 contacts the ejection portion 134 at the free end 138 thereof, the rotation of the bent portion 136 causes the retention portion 132 to deflect since movement of a mounting portion 131 end of the retention portion 132 is constrained by the mounting portion 131. Since the mounting portion 131 end of the retention portion 132 is constrained from moving, rotation of the bent portion 136 causes the retention portion 132 to deflect and bow away from the back plate 113 (or side surface of the receptacle 112) and towards the inserted battery 120 due to the curvature of the retention portion 132. The deflection of the retention portion 132 causes the retention portion 132 to come into contact with the battery 120, such as the side surface 123 of the battery 120, and the retention portion 132 exerts the retention force 132a on the side surface 123 of the battery 120, which prevents, or reduces, movement of the battery 120 within the battery receptacle 112. In the example of FIG. 2B, the retention and ejection forces 132a, 134a are shown as being oriented substantially orthogonal to each other, and each has a component of normal force that is perpendicular to the respective surface of the battery 120 that is contacted by the respective portions of the element 130. According to some examples, the depicted forces 132a, 134a of FIG. 2B represent components of retention and ejection forces that are oriented at different angles with respect to each other. These differently-oriented retention and ejection forces 132a, 134a are sufficient to prevent, or reduce, motion of the battery 120 within the battery receptacle 112 and to withdraw the battery 120 from the receptacle 112.

Figure 3:
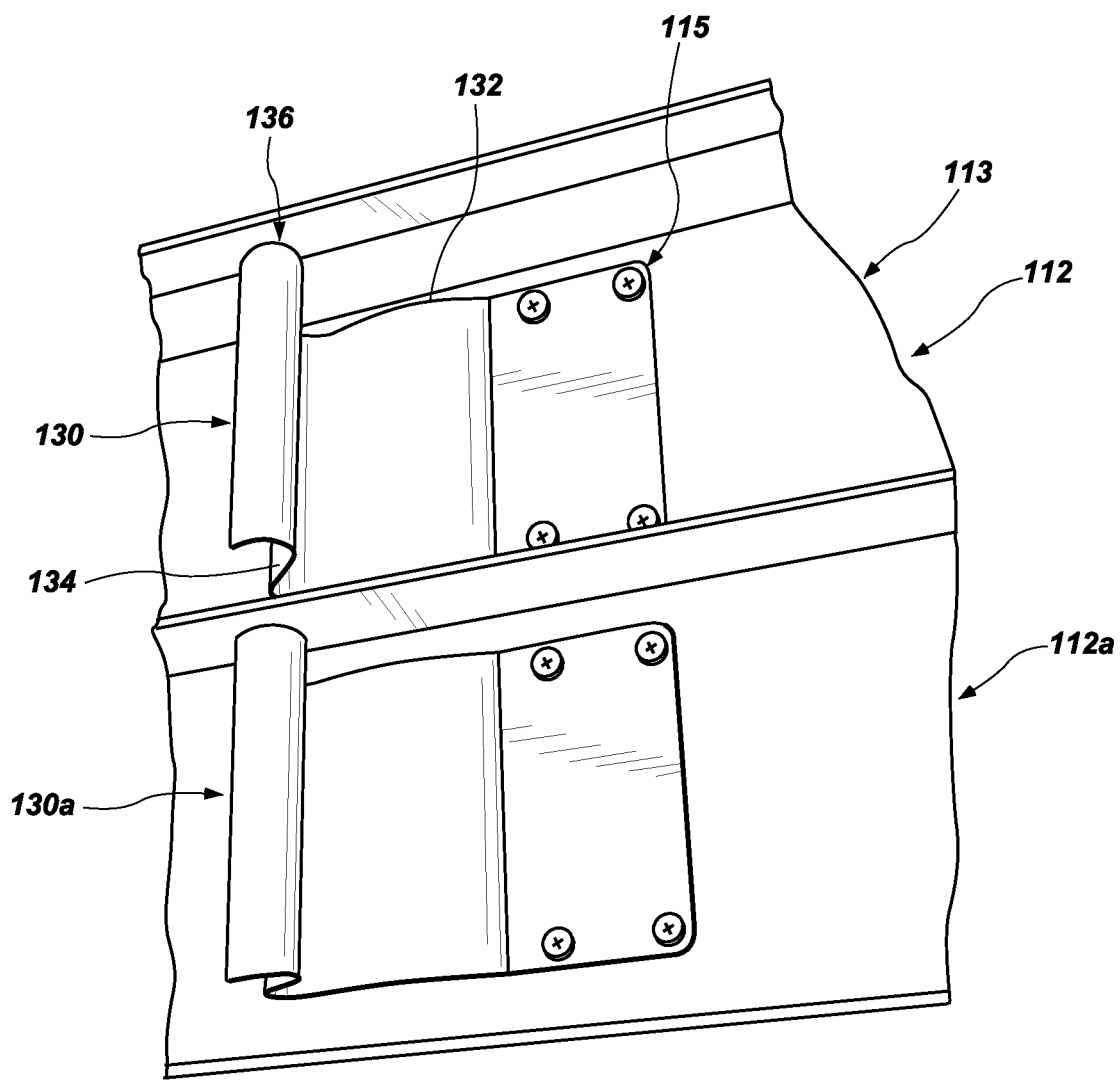
FIG. 3 illustrates a perspective view of a portion of an example back plate of a battery receptacle having an example set of battery retention and ejection elements.

FIG. 3 illustrates a perspective view of a portion of an example back plate 113 of a battery receptacle 112 having an example set of battery retention and ejection elements 130, 130a. In the example of FIG. 3, the medical device 110 includes two battery receptacles 112, 112a. The back plate 113 bounds a portion of the battery receptacles 112, 112a when the back plate 113 is coupled to the medical device 110. In the example of FIG. 3, when the back plate 113 is coupled to the medical device 110, the elements 130, 130a are positioned in respective battery receptacles 112, 112a. The elements 130, 130a are mounted to the back plate 113, which is part of, or mounted to, a side surface(s) of the receptacle(s) 112. The elements 130, 130a are aligned in a side-by-side manner, in the example of FIG. 3. In alternative examples, the elements 130, 130a are not aligned (e.g., the elements 130, 130a may be offset from one another in a direction into or out of the battery receptacles 112, 112a, depending on various factors like the overall position of the receptacles 112, 112a, the relative physical size of the batteries 120, and other factors.

In the example of FIG. 3, the mounting portion 131 of each of the elements 130, 130a has one or more holes (e.g., through holes) configured to receive one or more fasteners to mount the elements 130, 130a to the back plate 113. In FIG. 3, the fasteners include screws 115. In other examples, other fasteners (e.g., pins, bolts, etc.) are used to mount the elements 130, 130a to the back plate 113. According to some examples, the holes in mounting portions 131 of the elements 130, 130a and/or holes in the back plate 113 are threaded, or are configured to receive threaded inserts, and the threads allow the screws 115 or other threaded fasteners to be threaded into the holes to couple the elements 130, 130a to the back plate 113. By mounting of the elements 130, 130a to the back plate 113, the elements 130, 130a are configured to be decoupled from the back plate 113, such as to remove the elements 130, 130a for maintenance and repair, or to replace the elements 130, 130a. In an alternate example, the back plate 113 includes integral mounting studs onto which the through holes of the elements 130, 130a are placed to press-fit the elements 130, 130a to the back plate 113 of the battery receptacles 112, 112a.

Figure 4A:
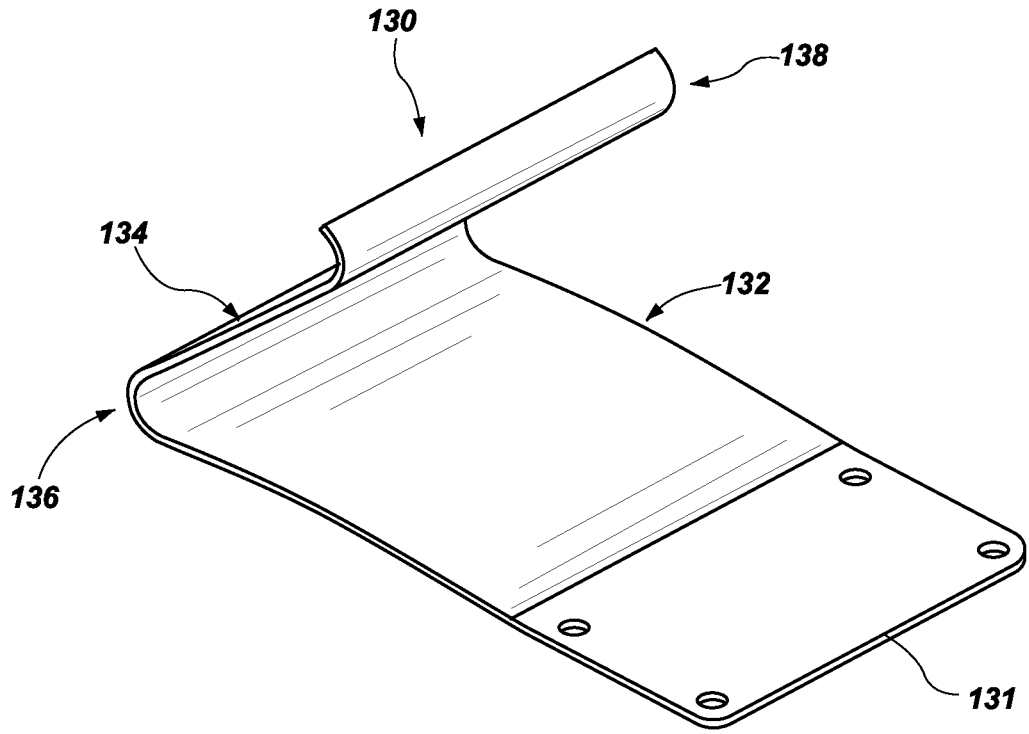
FIG. 4A illustrates a perspective view of an example battery retention and ejection element.
Figure 4B:
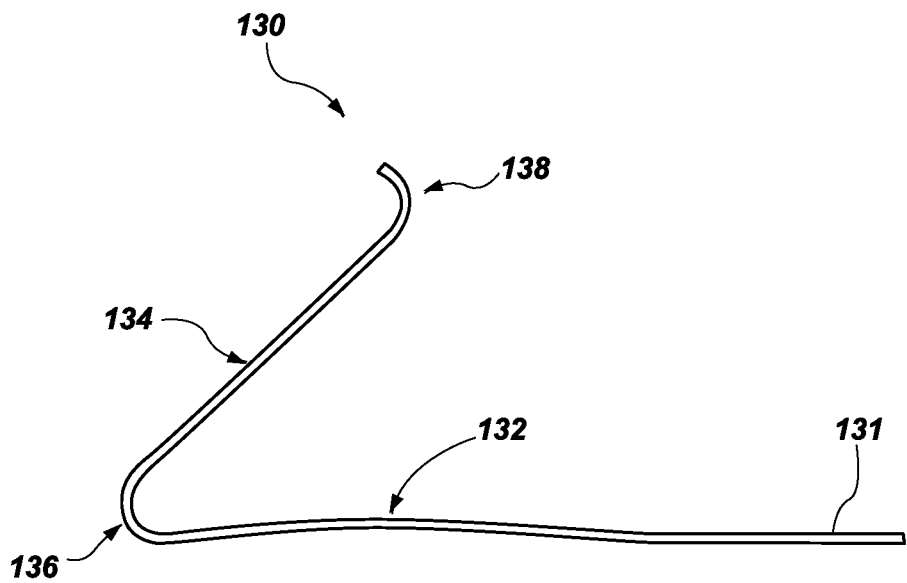
FIG. 4B illustrates a side view of the example battery retention and ejection element depicted in FIG. 4A.
Figure 4C:
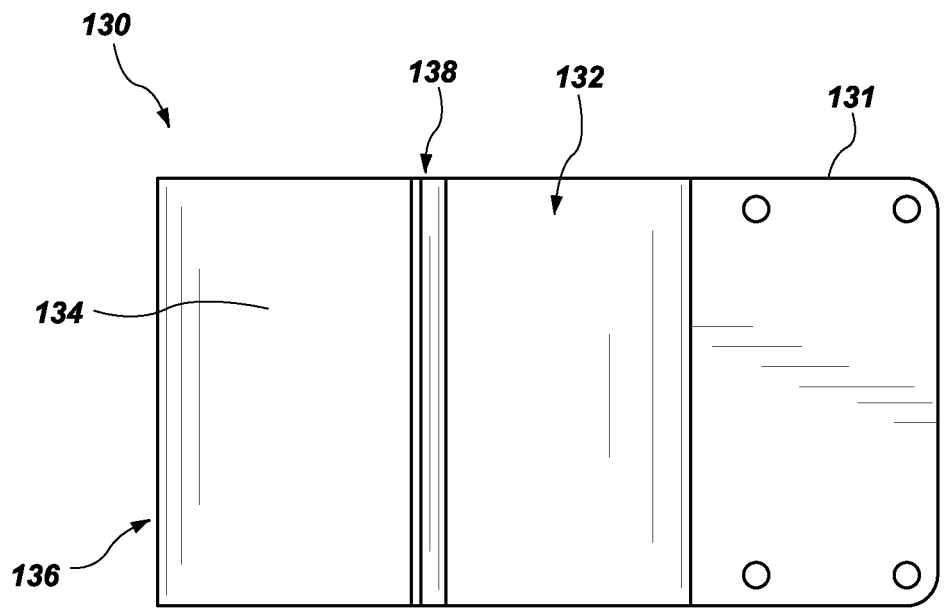
FIG. 4C illustrates a top view of the example battery retention and ejection element depicted in FIG. 4A.
Figure 4D:
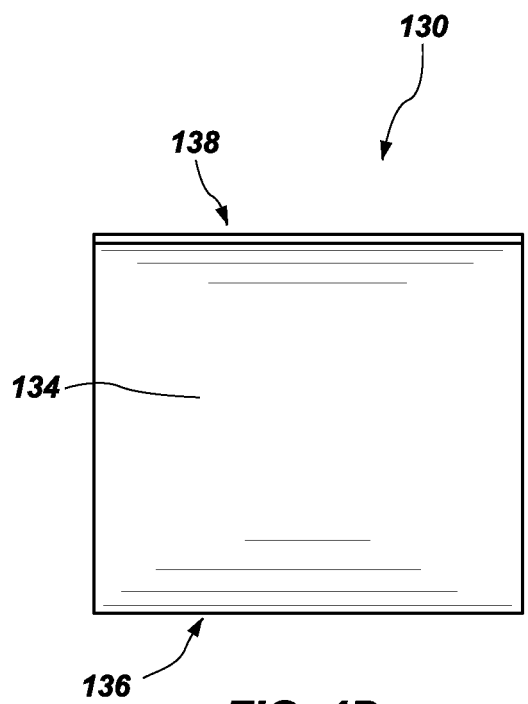
FIG. 4D illustrates a rear view of the example battery retention and ejection element depicted in FIG. 4A.
Figure 4E:
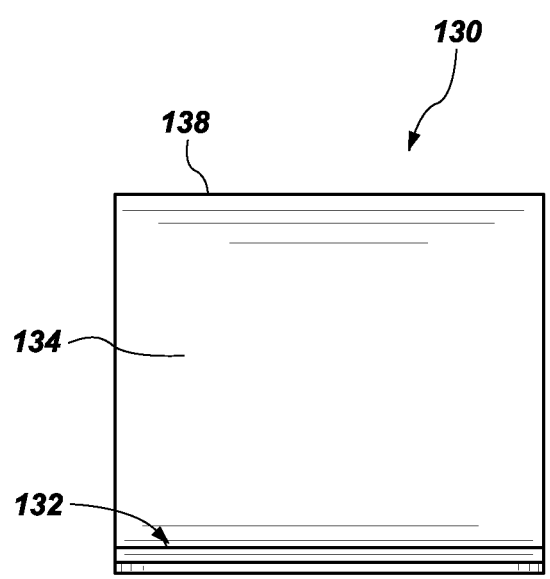
FIG. 4E illustrates a front view of the example battery retention and ejection element depicted in FIG. 4A.

FIG. 4A illustrates a perspective view of an example battery retention and ejection element, such as the element 130 depicted in FIGS. 2A-3. FIG. 4B illustrates a side view of the element 130 depicted in FIG. 4A, FIG. 4C illustrates a top view of the element 130 depicted in FIG. 4A, FIG. 4D illustrates a rear view of the element 130 depicted in FIG. 4A, and FIG. 4E illustrates a front view of the element 130 depicted in FIG. 4A. In the example of FIGS. 4A-4E, the element 130 is a leaf spring that is formed from as a single piece of material (e.g., a metal plate) using various shaping processes, such as bending. According to some examples, a strip of spring steel or other suitable material is used to form the element 130. In an example, the material used to form the element 130, or portions thereof, undergoes various treatments, such as heat-treating, to achieve the material property(ies) desired for the element 130. The material used to form the element 130 allows the element 130 to be deflected when a battery 120 is inserted into the battery receptacle 112 and when the battery 120 contacts and presses the element 130. As discussed above, the insertion of the battery 120 within the battery receptacle 112 causes the battery 120 to contact and press upon the element 130. This pressure of the battery 120 on the element 130 causes the element 130 to deflect from an initial state and to store potential energy in the form of the retention force 132a and the ejection force 134a. For example, each of the retention portion 132 and the ejection portion 134 are configured to deflect from an initial position when the battery 120 is inserted into the battery receptacle 112, and are biased to return to the initial position when the battery 120 is removed from the battery receptacle 112. Due to the material properties of the element 130 and the geometry of the element 130, the element 130 is biased to return to the initial state, such as shown in FIGS. 4A-4E. With the battery 120 is inserted into the battery receptacle 112 and secured therein, such as by a locking mechanism, the element 130 is prevented from returning to the initial state. The element 130 exerts the retention force 132a and the ejection force 134a when the element 130 is deflected by the inserted battery 120. According to some examples, a counter force, such as a force exerted by the locking mechanism, opposes the ejection force 134a to secure the battery 120 within the battery receptacle 112. When the counter force is released, such as by unlocking the locking mechanism (e.g., a user depressing the push button 122), the element 130 is biased to return to the initial state. Without the counter force, the ejection force 134*a* causes the battery 120 to be ejected from the open end of the battery receptacle 112.

The mounting portion 131 of the element 130 shown in FIG. 4A includes multiple holes (e.g., through holes) defined therein, which are usable to couple (e.g., mount) the element 130 to the battery receptacle 112, or portion thereof, such as the back plate 113 of the receptacle 112. According to some examples, fasteners are used to couple the element 130 to the battery receptacle 112, such as by inserting the fasteners into the through holes of the mounting portion 131 and fastening the fasteners. In other examples, the battery receptacle 112 includes elements, such as integral posts, onto which the through holes of the element 130 are configured to be placed, such as to press-fit the element 130 to the integral posts of the battery receptacle 112. In yet another example, hot staking is performed to partially melt the integral posts over the through holes of the element 130 to permanently couple the element 130 to the battery receptacle 112. The coupling of the element 130 to the battery receptacle 112 mounts (e.g., anchors) the element 130 within the battery receptacle 112. As used herein, the term "couple" may refer to an indirect coupling or a direct coupling between elements. The term "couple," as used herein, may also refer to a removable coupling or a permanent coupling between the elements. Elements are removably coupled if a user or another entity is able to decouple the elements. Elements are permanently coupled if a user or another entity is unable to decouple the elements without destroying or significantly damaging the elements, or without undue effort to dissemble the elements using tools or machinery. As used herein, the term "couple" can be interpreted as connect, attach, join, engage, interface, link, fasten, or bind. Unless otherwise specified herein, the term "couple" is to be interpreted as coupling elements in a mechanical sense, rather than in an electrical sense, for example. Nevertheless, it is to be appreciated that a mechanical coupling of elements may result in an electrical coupling(s) between multiple elements of the system.

FIG. 4B illustrates the bent shapes of the profile of the element 130. The retention portion 132 of the element 130 is configured to deflect so that the retention portion 132 bows away from a side wall of the battery receptacle 112. The curvature of the retention portion 132 shown in the example of FIG. 4B causes the deflection of the retention portion 132 in this direction. The curvature of the retention portion 132 is concave on a bottom surface of the element 130, and convex on a top surface of the element 130. The convex surface of the retention portion 132 faces the battery 120 when the battery 120 is inserted into the receptacle 112. The deflection of the retention portion 132 causes the retention portion 132 to contact the battery 120 (e.g., a side surface 123 of the battery 120), which prevents, or reduces, motion (e.g., transverse motion, longitudinal motion, or a combination thereof) of the battery 120 within, and relative to, the battery receptacle 112.

The bent portion 136 of the element 130 shown in FIG. 4B is interposed between the retention portion 132 and the ejection portion 134, and the bent portion 136 has a radius of curvature that is formed by bending the material of the element 130 into the shape of the bent portion 136 depicted in FIG. 4B. The curvature of the bent portion 136 is concave on the top surface of the element 130, and convex on the bottom surface of the element 130. The concave surface of the bent portion 136 faces the battery 120 when the battery 120 is inserted into the receptacle 112. The bent portion 136 causes the ejection portion 134 of the element 130 to be oriented at a first (e.g., acute) angle relative to the retention portion 132 of the element 130 when the element 130 is in the initial state, such as shown in FIGS. 4A-4E. When a battery 120 comes into contact with, and presses, the element 130 at the free end 138 of the element 130, the bent portion 136 substantially maintains the radius of curvature, and the ejection portion 134 deflects such that the ejection portion 134 is oriented at a second angle relative to the retention portion 132, such as the second angle shown in FIG. 2B, the second angle greater than the first angle. By substantially maintaining the radius of curvature, the bent portion 136 rotates relative to the retention portion 132 when the battery 120 is pressed against the ejection portion 134, which causes the deflection of the retention portion 132, such as shown in FIG. 2B.

The ejection portion 134 of the element 130 terminates in the free end 138. The battery 120, when inserted into the battery receptacle 112 where the element 130 is positioned, contacts and presses the free end 138 of the ejection portion 134, which causes the free end 138 to be displaced further into the battery receptacle 112. The displacement of the free end 138 causes the ejection portion 134 to be rotated about a fulcrum at the bent portion 136. The ejection portion 134 rotates from a first angle relative to the retention portion 132 to a second angle relative to the retention portion 132, the second angle greater than the first angle. This movement of the ejection portion 134 also causes the element 130 to store potential energy as the element 130 is changed from the initial state, such as shown in FIGS. 2A and 4A-4E, to a deflected state, such as shown in FIG. 2B. The rolled lip of the free end 138 provides a rounded surface the battery 120 is configured to engage, which prevents the battery 120 from being damaged or caught by the element 130.

Figure 5A:
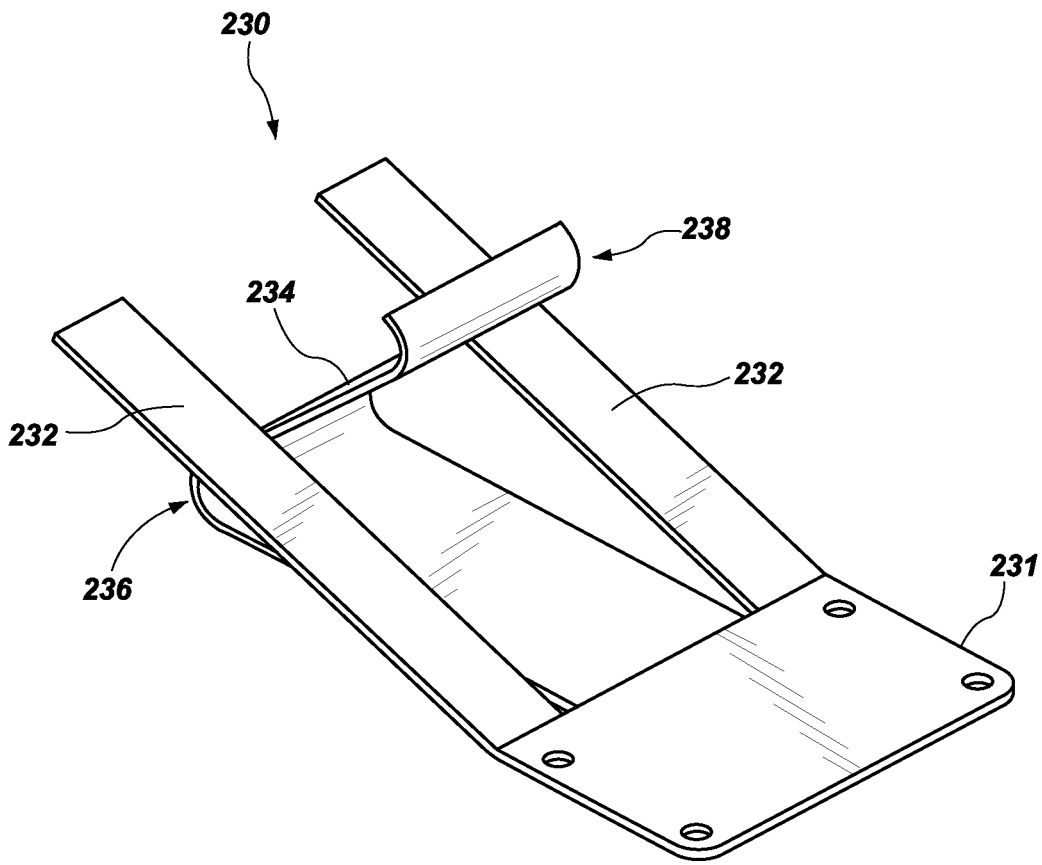
FIG. 5A illustrates a perspective view of another example battery retention and ejection element.
Figure 5B:
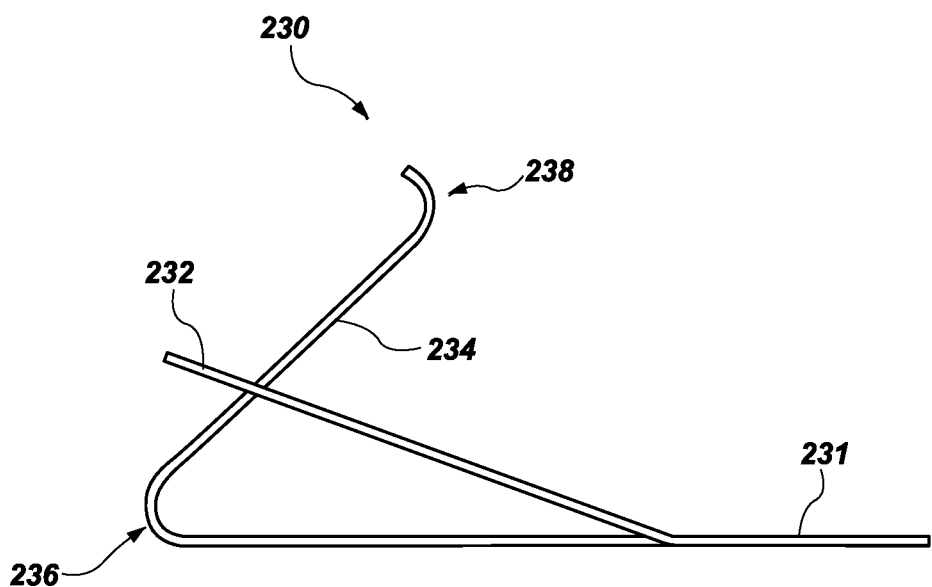
FIG. 5B illustrates a side view of the example battery retention and ejection element depicted in FIG. 5A.
Figure 5C:
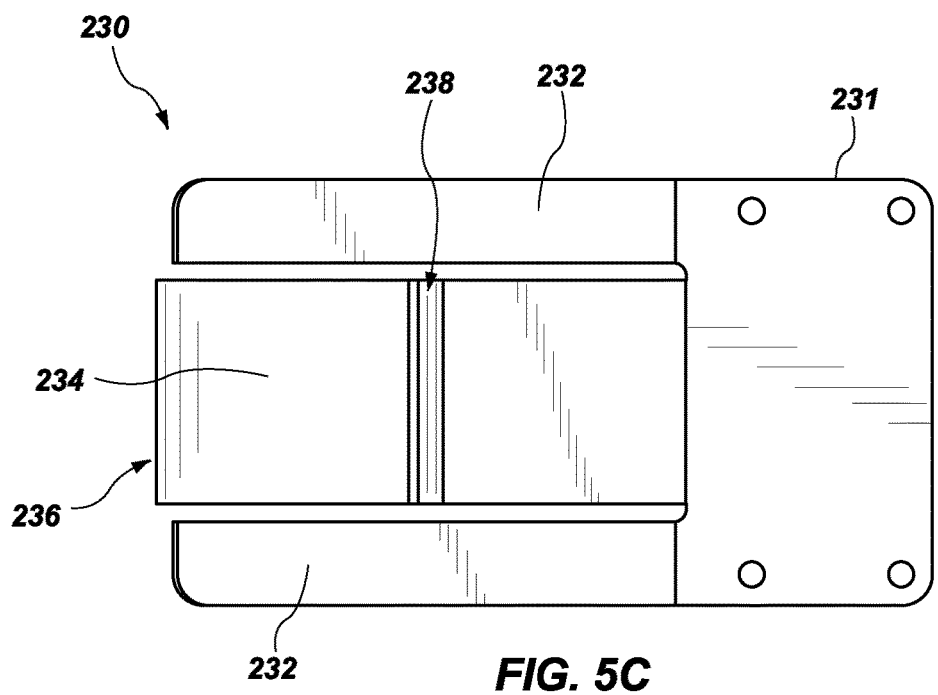
FIG. 5C illustrates a top view of the example battery retention and ejection element depicted in FIG. 5A.
Figure 5D:
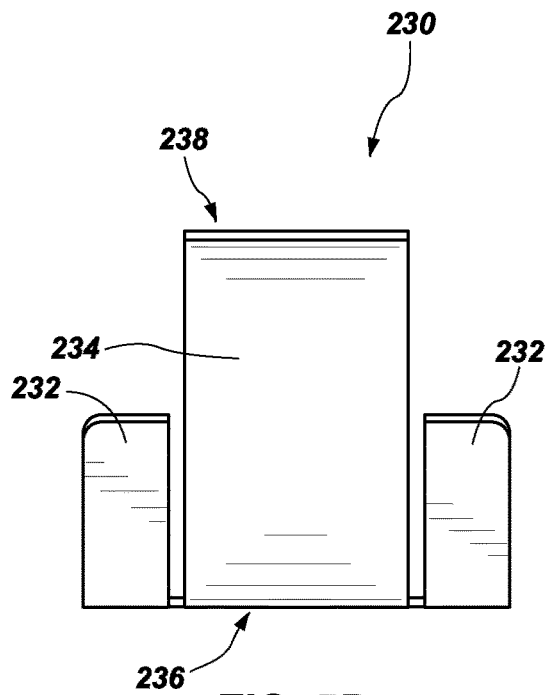
FIG. 5D illustrates a rear view of the example battery retention and ejection element depicted in FIG. 5A.
Figure 5E:
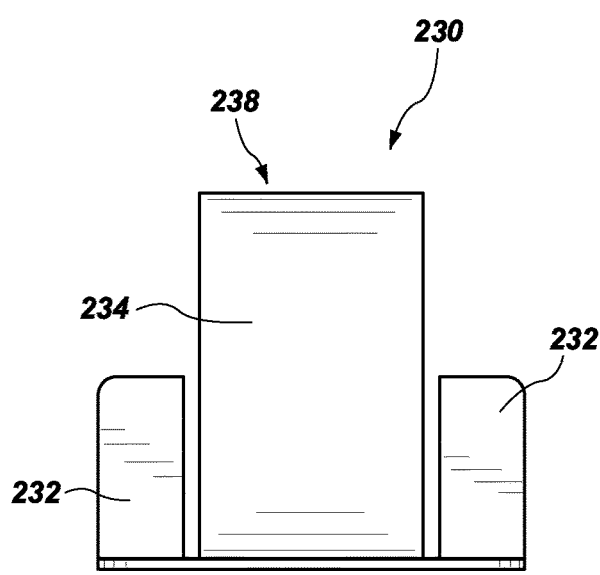
FIG. 5E illustrates a front view of the example battery retention and ejection element depicted in FIG. 5A.

FIG. 5A is perspective view of another example battery retention and ejection element 230 (sometimes referred to herein as an "element" or a "spring") in an initial state. FIG. 5B illustrates a side view of the element 230 depicted in FIG. 5A, FIG. 5C illustrates a top view of the element 230 depicted in FIG. 5A, FIG. 5D illustrates a rear view of the element 230 depicted in FIG. 5A, and FIG. 5E illustrates a front view of the element 230 depicted in FIG. 5A. Similar to the battery retention and ejection element 130 of FIGS. 4A-4E, the battery retention and ejection element 230 of FIGS. 5A-5E is configured to retain the battery 120 within the battery receptacle 112 and to eject the battery 120 from the battery receptacle 112. The element 230 depicted in FIGS. 5A-5E includes a mounting portion 231, a retention portion 232, a bent portion 236, and an ejection portion 234 terminating in a free end 238. The mounting portion 231, bent portion 236, ejection portion 234, and free end 238 of the element 230 are similar to the respective mounting portion 131, bent portion 136, ejection portion 134, and free end 138 of the element 130 of FIGS. 4A-4E. For the sake of brevity, these portions 231, 236, 234, and 238 are not described in detail, as reference can be made to the portions 131, 136, 134, and 138 of the element 130 to understand their form and function. For example, these similar portions 231, 236, 234, and 238 of the element 230 perform similar functions to the functions performed by the portions 131, 136, 134, and 138 of the element 130, such as helping to remove the battery 120 from the battery receptacle 112 by exerting an ejection force, such as the ejection force 134*a* of FIG. 2B, on the battery 120.

The retention portion 232 (sometimes referred to herein in the plural as "retention portions 232") of the element 230 is similar in function to the retention portion 132 of the element 230 in that the retention portion 232 is also configured to exert a retention force, such as the retention force 132a, on the battery 120 when the battery 120 is engaged with the element 230. In the example of FIGS. 5A-5E, the retention portion 232 includes a pair of flat springs, one on each side of the element 230. Each flat spring of the retention portion 232 extends at an angle from the mounting portion 231 at a side wall of the battery receptacle 112 and terminates at an additional free end near the center of the battery receptacle 112 cavity. The retention portion 232 (e.g., the additional free end of each flat, angled spring) is configured to contact a surface (e.g., the side surface 123) of the battery 120 when the battery 120 is inserted into the receptacle 112, and to compress and clamp the battery 120 against an opposing side surface of the battery receptacle 112 due to the exerted retention force. Similar to the retention force 132a of FIG. 2B, the retention force exerted by the retention portion 232 of the element 230 helps prevent motion (e.g., lateral motion, longitudinal motion, or a combination thereof) of a battery 120 within, and relative to, a battery receptacle 112. Due to the pair of flat, angled springs of the retention portion 232, the retention portion 232 is configured to exert the retention force at two locations on the surface (e.g., the side surface 123) of the battery 120, resulting in two retention forces exerted on the battery 120.

Figure 6A:
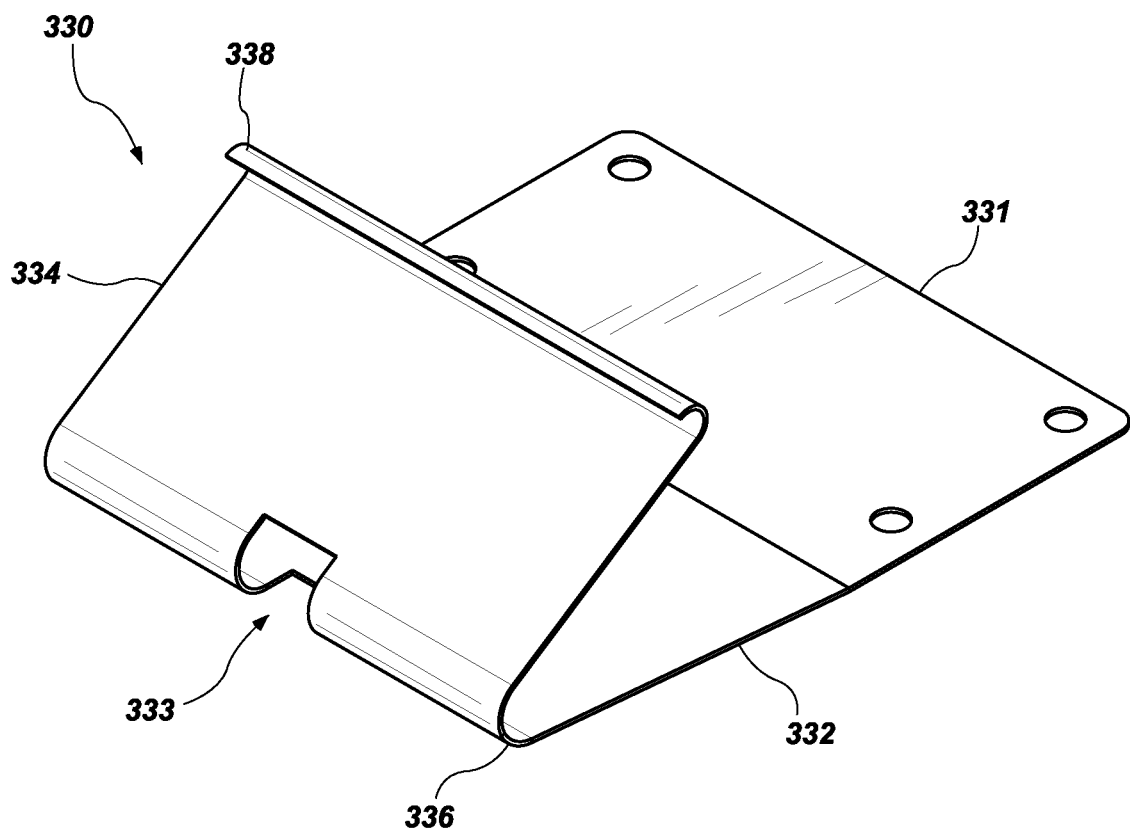
FIG. 6A illustrates a perspective view of another example battery retention and ejection element.
Figure 6B:
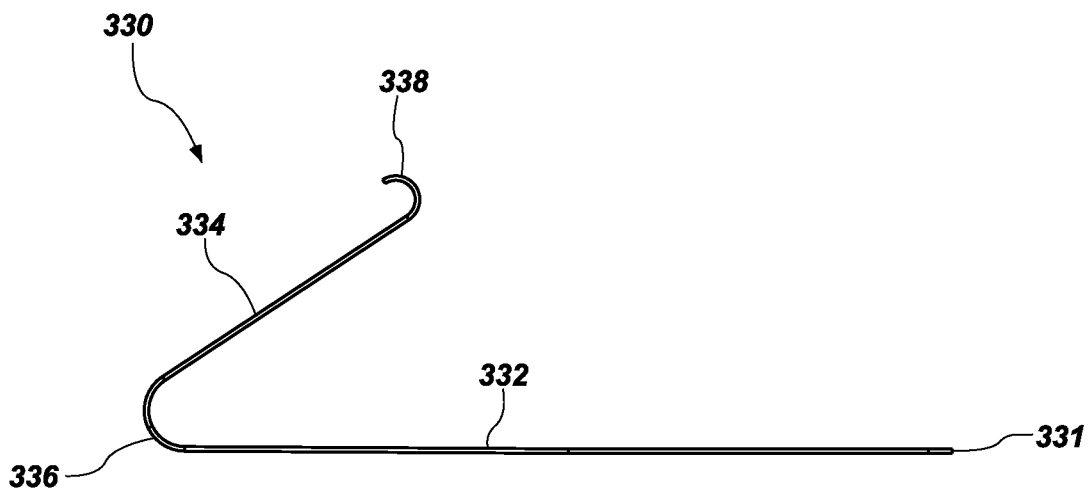
FIG. 6B illustrates a side view of the example battery retention and ejection element depicted in FIG. 6A.
Figure 6C:
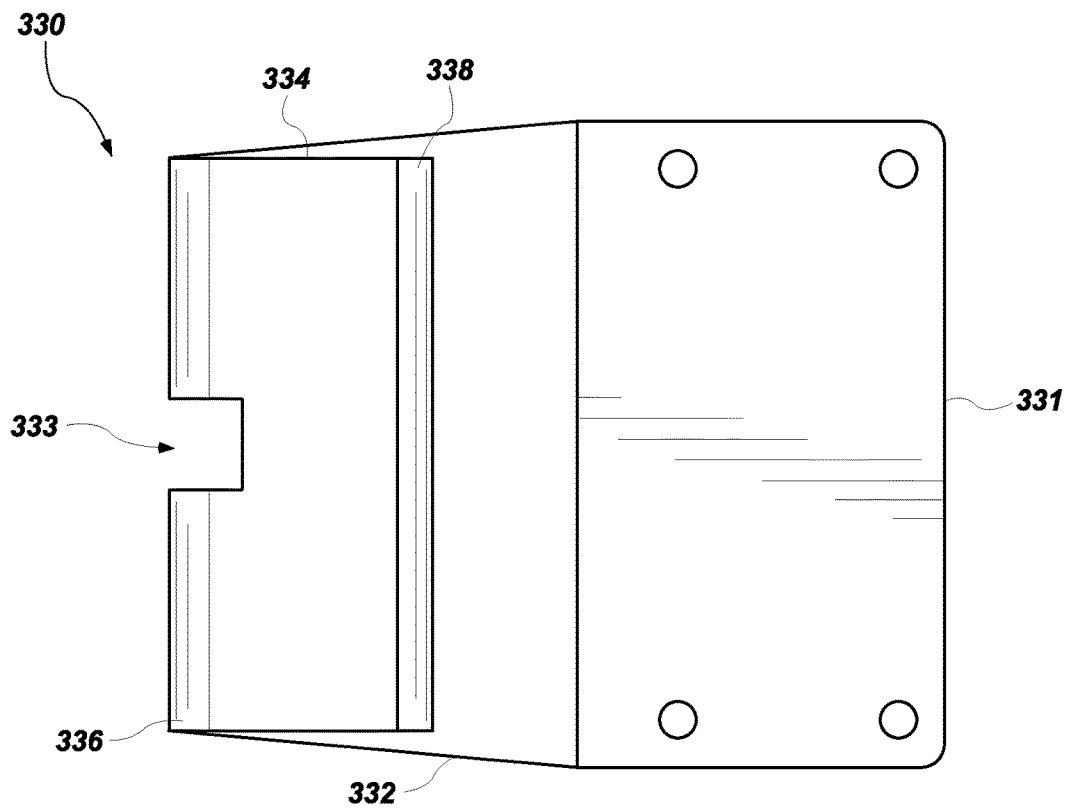
FIG. 6C illustrates a top view of the example battery retention and ejection element depicted in FIG. 6A.
Figure 6D:
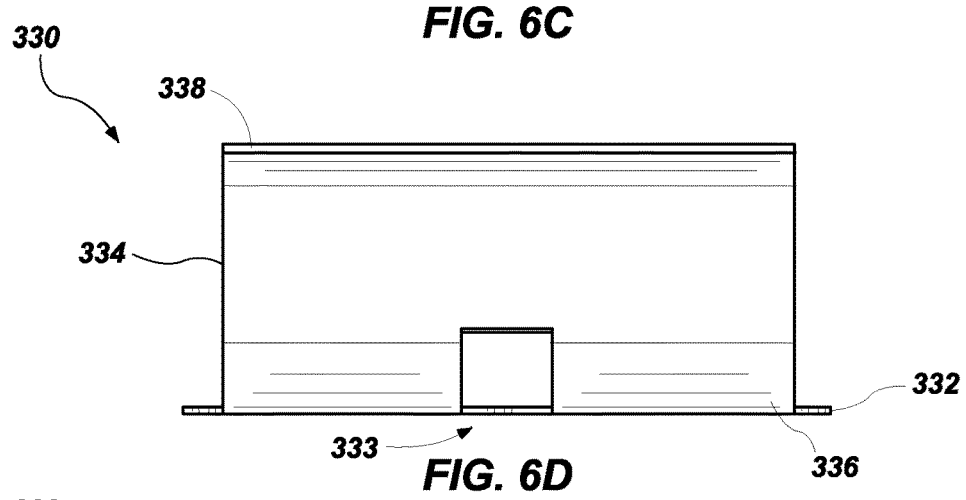
FIG. 6D illustrates a rear view of the example battery retention and ejection element depicted in FIG. 6A.
Figure 6E:
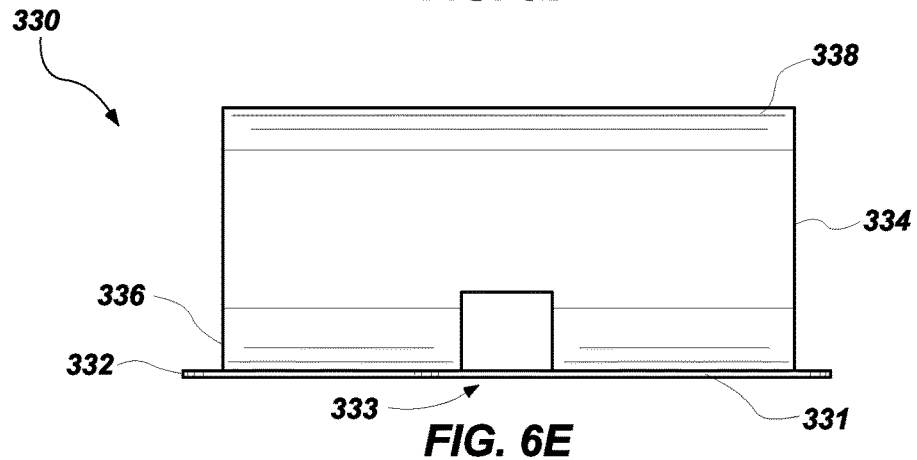
FIG. 6E illustrates a front view of the example battery retention and ejection element depicted in FIG. 6A.

FIG. 6A illustrates a perspective view of another example battery retention and ejection element 330 (sometimes referred to herein as an "element" or a "spring") in an initial state. FIG. 6B illustrates a side view of the element 330 depicted in FIG. 6A, FIG. 6C illustrates a top view of the element 330 depicted in FIG. 6A, FIG. 6D illustrates rear view of the element 330 depicted in FIG. 6A, and FIG. 6E illustrates a front view of the element 330 depicted in FIG. 6A. Similar to the battery retention and ejection element 130 of FIGS. 4A-4E and the element 230 of FIGS. 5A-5E, the battery retention and ejection element 330 of FIGS. 6A-6E is configured to retain the battery 120 within the battery receptacle 112 and to eject the battery 120 from the battery receptacle 112. The element 330 includes a mounting portion 331, a retention portion 332, a bent portion 336, and an ejection portion 334 having a free end 338. The mounting portion 331, ejection portion 334, and free end 338 of the element 330 are similar to the respective mounting portions 131, 231, ejection portions 134, 234, and free ends 138, 238 of the elements 130 and 230 of FIGS. 4A-4E and of FIGS. 5A-5E, respectively. For the sake of brevity, these portions 331, 334, and 338 are not described in detail, as reference can be made to the portions 131, 134, and 138 of the element 130 to understand their form and function. For example, these similar portions 331, 334, and 338 of the element 330 perform similar functions to the functions performed by the portions 131, 134, and 138 of the element 130, such as helping to remove the battery 120 from the battery receptacle 112 by exerting an ejection force, such as the ejection force 134a of FIG. 2B, on the battery 120.

The retention portion 332 of the element 330 is similar in function to the retention portion 132 of the element 130 of FIGS. 4A-4E. However, the retention portion 332 of the element 330 differs from the retention portion 132 in that the retention portion 332 of the element 330 is substantially planer without a curvature in the profile of the retention portion 332, and the retention portion 332 of the element 330 also tapers lengthwise along the element 330 from the mounting portion 331 to the bent portion 336 so that a width of the bent portion 336 and ejection portion 334 are narrower than the width of the mounting portion 331. Furthermore, the bent portion 336 of the element 330 includes an opening 333 (sometimes referred to herein as a "cutout") defined in the center of the bent portion 336.

Figure 7:
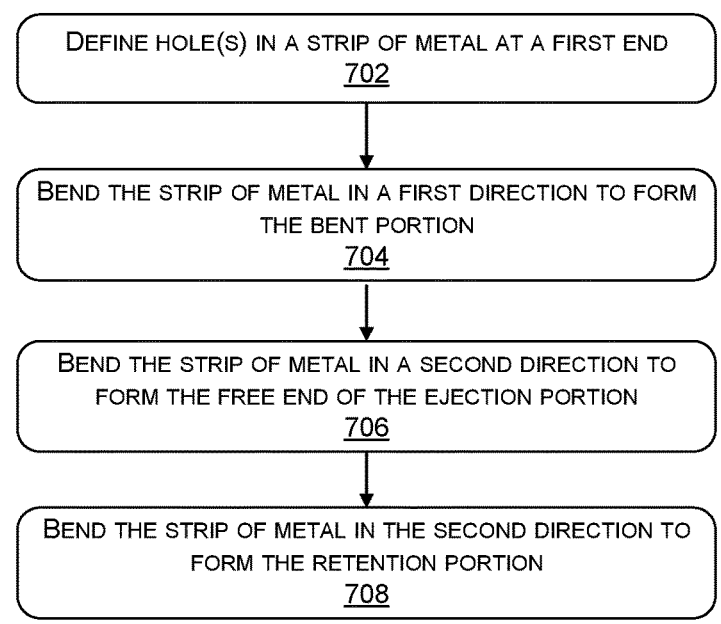
FIG. 7 illustrates an example process for forming a battery retention and ejection element.
Figure 8:
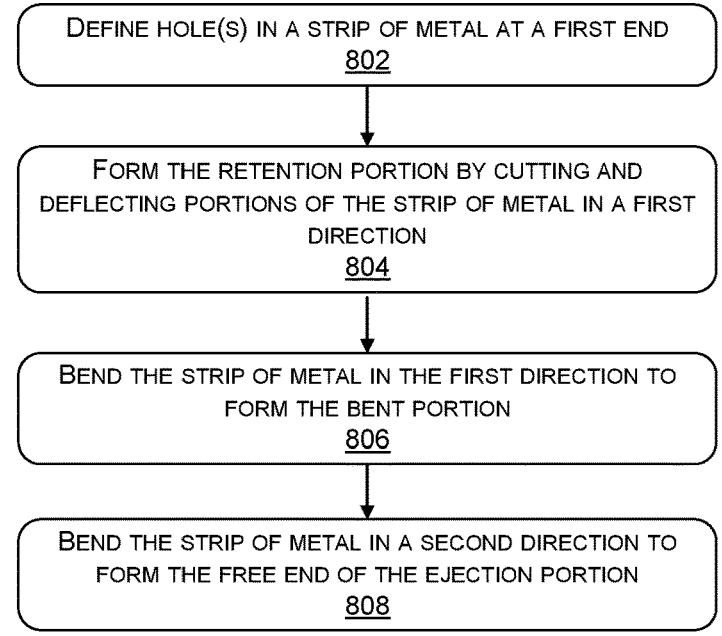
FIG. 8 illustrates another example process for forming a battery retention and ejection element.
Figure 9:
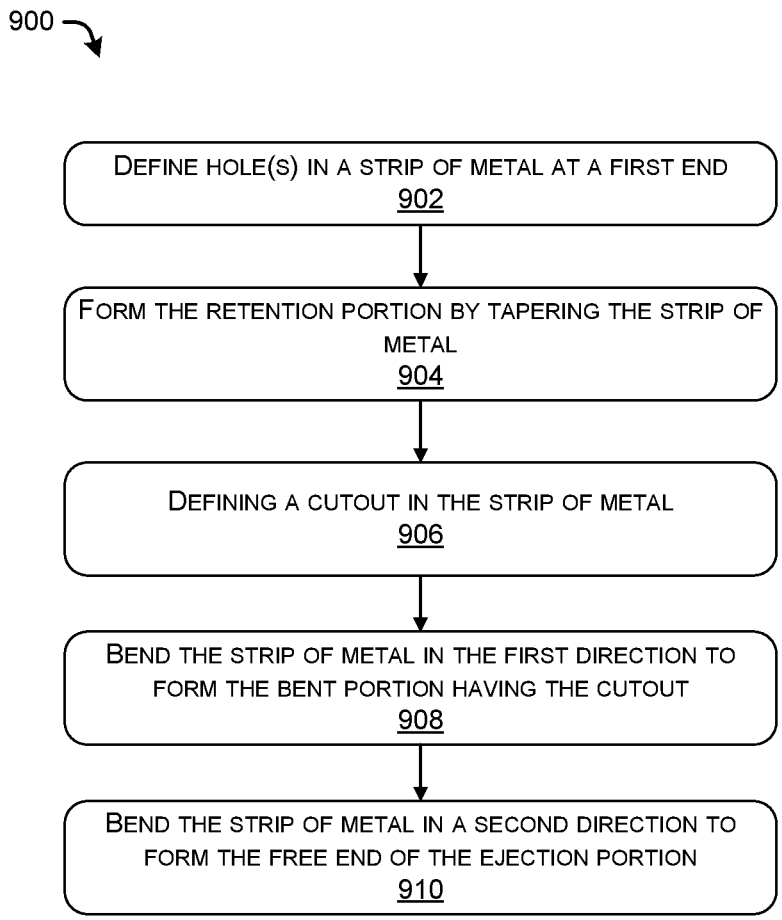
FIG. 9 illustrates another example process for forming a battery retention and ejection element.

FIGS. 7-9 illustrate an example processes related to various implementations of the present disclosure. Although FIGS. 7-9 illustrate separate processes, in various examples, a single entity can perform any combination of the processes. Furthermore, although FIGS. 7-9 illustrate steps in a particular order, implementations are not limited to the specific order of operations illustrated in the figures. In various implementations, the processes are performed by an entity(ies) involved in manufacturing or assembling a battery retention and ejection element to be disposed in a battery receptacle 112 of a medical device 110. According to some examples, the entity(ies) that perform the processes include a human, a robot or other autonomous machinery configured to form the element, a medical device 110, or any combination thereof.

FIG. 7 illustrates an example process 700 for forming a battery retention and ejection element, such as the element 130 depicted in FIGS. 2A-4E. At 702, one or more holes are defined in a strip of metal at a first end of the strip of metal. According to some examples, the metal is steel (e.g., spring steel). According to some examples, the one or more holes include a plurality of holes, such as four holes. In an illustrative example, one or more first holes of the plurality of holes are defined (e.g., machined) in the strip of metal on a first side of the strip of metal at the first end, and one or more second holes of the plurality of holes are defined (e.g., machined) in the strip of metal on a second side of the strip of metal at the first end.

At 704, the strip of metal is bent in a first direction at a first location between the first end of the strip of metal and a second end of the strip of metal to form a bent portion 136 of the element 130 having a first curvature and an ejection portion 134 of the element 130 between the bent portion 136 and the second end of the strip of metal. According to some examples, the bending of the strip of metal in the first direction at block 704 includes bending the strip of metal such that the second end of the strip of metal is rotated about a fulcrum by more than 90 degrees to orient the ejection portion 134 at an acute angle relative to the (to-be-formed) retention portion 132.

At 706, the strip of metal is bent in a second direction opposite the first direction at the second end of the strip of metal to form a free end 138 of the ejection portion 134, the free end 138 having a second curvature. This forms a free end 138 with a rolled lip to prevent the element 130 catching on an inserted battery 120 during removal of the battery 120.

At 708, the strip of metal is bent in the second direction at a second location between the bent portion 136 and the first end of the strip of metal to form a retention portion 132 of the element 130 having a third curvature. The bending at block 708 is minimal to form a slight curvature in the retention portion 132, as shown in FIG. 4B.

FIG. 8 illustrates another example process 800 for forming a battery retention and ejection element, such as the element 230 depicted in FIGS. 5A-5E. At 802, one or more holes are defined in a strip of metal at a first end of the strip of metal. According to some examples, the metal is steel (e.g., spring steel). According to some examples, the one or more holes include a plurality of holes, such as four holes. In an illustrative example, one or more first holes of the plurality of holes are defined (e.g., machined) in the strip of metal on a first side of the strip of metal at the first end, and one or more second holes of the plurality of holes are defined (e.g., machined) in the strip of metal on a second side of the strip of metal at the first end.

At 804, a retention portion 232 is formed from the strip of metal as a pair of flat, angled springs on each side of the strip of metal. For example, block 804 includes forming a first flat spring on a first side of the strip of metal by cutting the strip of metal lengthwise along the strip of metal from a second end of the strip of metal to a first point that is a distance from the first end of the strip of metal. Block 804 further includes forming a second flat spring on a second side of the strip of metal by cutting the strip of metal lengthwise along the strip of metal from the second end of the strip of metal to a second point that is the distance from the first end of the strip of metal. Block 804 further includes deflecting, in a first direction, the first flat spring at the first point and the second flat spring at the second point to form a retention portion 232 of the element 230 that includes a pair of flat springs that are angled relative to a remainder of the strip of metal.

At 806, the strip of metal is bent in the first direction at a first location between the first end of the strip of metal and a second end of the strip of metal to form a bent portion 236 of the element 230 having a first curvature and an ejection portion 234 of the element 230 between the bent portion 236 and the second end of the strip of metal. According to some examples, the bending of the strip of metal in the first direction at block 806 includes bending the strip of metal such that the second end of the strip of metal is rotated about a fulcrum by more than 90 degrees.

At 808, the strip of metal is bent in a second direction opposite the first direction at the second end of the strip of metal to form a free end 238 of the ejection portion 234, the free end 238 having a second curvature. This forms a free end 238 with a rolled lip to prevent the element 230 catching on an inserted battery 120 during removal of the battery 120.

FIG. 9 illustrates another example process 900 for forming a battery retention and ejection element, such as the element 330 depicted in FIGS. 6A-6E. At 902, one or more holes are defined in a strip of metal at a first end of the strip of metal. According to some examples, the metal is steel (e.g., spring steel). According to some examples, the one or more holes include a plurality of holes, such as four holes. In an illustrative example, one or more first holes of the plurality of holes are defined (e.g., machined) in the strip of metal on a first side of the strip of metal at the first end, and one or more second holes of the plurality of holes are defined (e.g., machined) in the strip of metal on a second side of the strip of metal at the first end.

At 904, the strip of metal is tapered by cutting off part of a first side of the strip of metal at a second end of the strip of metal and by cutting off part of a second side of the strip of metal at the second end of the strip of metal. This forms a substantially planar retention portion 332 of the element 330. At 906, a cutout is defined in the strip of metal at a first location between the first end of the strip of metal and the second end of the strip of metal.

At 908, the strip of metal is bent in a first direction at a first location where the cutout is defined between the first end of the strip of metal and a second end of the strip of metal to form a bent portion 336 of the element 330 having a first curvature and an ejection portion 334 of the element 330 between the bent portion 336 and the second end of the strip of metal. According to some examples, the bending of the strip of metal in the first direction at block 908 includes bending the strip of metal such that the second end of the strip of metal is rotated about a fulcrum by more than 90 degrees to orient the ejection portion 334 at an acute angle relative to the (to-be-formed) retention portion 332.

At 910, the strip of metal is bent in a second direction opposite the first direction at the second end of the strip of metal to form a free end 338 of the ejection portion 334, the free end 338 having a second curvature. This forms a free end 338 with a rolled lip to prevent the element 330 catching on an inserted battery 120 during removal of the battery 120.

EXAMPLE CLAUSES

1. A portable defibrillator including: a battery receptacle configured to receive a battery; and an element positioned within the battery receptacle, the element including: a retention portion positioned at a side wall of the battery receptacle and configured to contact, and exert a retention force on, a side surface of the battery when the battery is inserted into the battery receptacle; an ejection portion that terminates in a free end positioned a distance from the side wall, wherein the free end of the ejection portion has a rolled lip and is configured to contact, and exert an ejection force on, an end surface of the battery when the battery is inserted into the battery receptacle; a bent portion interposed between the retention portion and the ejection portion, the bent portion causing the ejection portion to be oriented at an acute angle relative to the retention portion prior to insertion of the battery into the battery receptacle; and a mounting portion configured to mount the element to the side wall of the battery receptacle via a hole defined in the mounting portion, wherein the retention portion is interposed between the mounting portion and the bent portion.
2. A medical device including: a battery receptacle configured to receive a battery; and an element positioned within the battery receptacle, the element including: a retention portion positioned at a side wall of the battery receptacle and configured to contact, and exert a retention force on, a side surface of the battery when the battery is inserted into the battery receptacle; and an ejection portion that terminates in a free end positioned a distance from the side wall, the free end of the ejection portion configured to contact, and exert an ejection force on, an end surface of the battery when the battery is inserted into the battery receptacle.
3. The medical device of clause 2, wherein the element is a monolithic structure.
4. The medical device of clause 2 or 3, wherein: the element further includes a bent portion interposed between the retention portion and the ejection portion; and the ejection portion is oriented at an acute angle relative to the retention portion prior to insertion of the battery into the battery receptacle.
5. The medical device of clause 4, wherein: the element further includes a mounting portion configured to mount the element to the side wall of the battery receptacle; and the retention portion is interposed between the mounting portion and the bent portion.
6. The medical device of any one of clauses 2 to 5, wherein the retention portion: has a curvature; and is configured to deflect away from the side wall of the battery receptacle in response to a deflection of the free end of the ejection portion when the battery is inserted into the battery receptacle.
7. The medical device of any one of clause 2 or 3, wherein: the element further includes a mounting portion configured to mount the element to the side wall of the battery receptacle; and the retention portion includes a pair of flat springs, each flat spring of the pair of flat springs extending at an angle from the mounting portion at the side wall of the battery receptacle and terminating at an additional free end.

8. The medical device of any one of clauses 2 to 7, wherein the retention portion and the ejection portion are each: configured to deflect from an initial position when the battery is inserted into the battery receptacle; and biased to return to the initial position when the battery is removed from the battery receptacle.
9. The medical device of any one of clauses 2 to 8, wherein the medical device is a defibrillator.
10. An element configured to be disposed within a battery receptacle of a medical device, the element including: a retention portion to be positioned at a side wall of the battery receptacle, the retention portion configured to contact the battery and to exert a retention force on the battery in a first direction when the battery is inserted into the battery receptacle; and an ejection portion that terminates in a free end to be positioned a distance from the side wall of the battery receptacle, the free end of the ejection portion configured to contact the battery and to exert an ejection force on the battery in a second direction different than the first direction when the battery is inserted into the battery receptacle.
11. The element of clause 10, further including a bent portion interposed between the retention portion and the ejection portion, wherein the ejection portion is oriented at a first angle relative to the retention portion.
12. The element of clause 11, wherein: the free end of the ejection portion is movable; and the ejection portion is configured to be oriented at a second angle relative to the retention portion when the battery is inserted into the battery receptacle, the second angle greater than the first angle.
13. The element of any one of clauses 10 to 12, further including a mounting portion configured to mount the element within the battery receptacle, wherein the retention portion is interposed between the mounting portion and the bent portion.
14. The element of any one of clauses 10 to 13, wherein the retention portion: has a curvature; and is configured to deflect away from the side wall of the battery receptacle in response to a deflection of the free end of the ejection portion when the battery is inserted into the battery receptacle.
15. The element of any one of clauses 10 to 14, wherein the element is a monolithic structure.
16. The element of clause 15, wherein the monolithic structure is made of spring steel.
17. The element of clause 10, 15, or 16, further including a mounting portion configured to mount the element within the battery receptacle, wherein the retention portion includes a pair of flat springs, each flat spring of the pair of flat springs extending at an angle from the mounting portion at the side wall of the battery receptacle and terminating at an additional free end.
18. The element of any one of clauses 10 to 17, wherein the retention portion and the ejection portion are each: configured to deflect from an initial position when the battery is inserted into the battery receptacle; and biased to return to the initial position when the battery is removed from the battery receptacle.
19. The element of any one of clauses 10 to 18, wherein the medical device is portable.
20. A method of forming an element to be disposed within a battery receptacle of a medical device, the method including: defining a hole in a strip of metal at a first end of the strip of metal; bending the strip of metal in a first direction at a first location between the first end of the strip of metal and a second end of the strip of metal to form a bent portion of the element having a first curvature and an ejection portion of the element between the bent portion and the second end of the strip of metal; bending the strip of metal in a second direction opposite the first direction at the second end of the strip of metal to form a free end of the ejection portion, the free end having a second curvature; and bending the strip of metal in the second direction at a second location between the bent portion and the first end of the strip of metal to form a retention portion of the element having a third curvature.
21. The method of clause 20, wherein the bending of the strip of metal in the first direction includes bending the strip of metal such that the second end is rotated about a fulcrum by more than 90 degrees to orient the ejection portion at an acute angle relative to the retention portion.
22. The method of clause 20 or 21, wherein the metal includes steel.
23. The method of any one of clauses 20 to 22, wherein the hole is a first hole, and wherein the defining includes: machining the first hole in the strip of metal on a first side of the strip of metal; and machining a second hole in the strip of metal on a second side of the strip of metal.
24. The method of any one of clauses 20 to 23, wherein the medical device is a portable defibrillator.
25. A method of forming an element to be disposed within a battery receptacle of a medical device, the method including: defining a hole in a strip of metal at a first end of the strip of metal; forming a first flat spring on a first side of the strip of metal by cutting the strip of metal lengthwise along the strip of metal from a second end of the strip of metal to a first point that is a distance from the first end of the strip of metal; forming a second flat spring on a second side of the strip of metal by cutting the strip of metal lengthwise along the strip of metal from the second end of the strip of metal to a second point that is the distance from the first end of the strip of metal; deflecting, in a first direction, the first flat spring at the first point and the second flat spring at the second point to form a retention portion of the element that includes a pair of flat springs that are angled relative to a remainder of the strip of metal; bending the strip of metal in the first direction at a first location between the first end of the strip of metal and the second end of the strip of metal to form a bent portion of the element having a first curvature and an ejection portion of the element between the bent portion and the second end of the strip of metal; and bending the strip of metal in a second direction opposite the first direction at the second end of the strip of metal to form a free end of the ejection portion, the free end having a second curvature.
26. The method of clause 25, wherein the bending of the strip of metal in the first direction includes bending the strip of metal such that the second end is rotated about a fulcrum by more than 90 degrees.
27. The method of clause 25 or 26, wherein the metal includes steel.
28. The method of any one of clauses 25 to 27, wherein the hole is a first hole, and wherein the defining includes: machining the first hole in the strip of metal on the first side of the strip of metal; and machining a second hole in the strip of metal on the second side of the strip of metal.

29. A method of forming an element to be disposed within a battery receptacle of a medical device, the method including: defining a hole in a strip of metal at a first end of the strip of metal; tapering the strip of metal by cutting off part of a first side of the strip of metal at a second end of the strip of metal and by cutting off part of a second side of the strip of metal at the second end of the strip of metal; defining a cutout in the strip of metal at a first location between the first end of the strip of metal and the second end of the strip of metal; bending the strip of metal in a first direction at the first location to form a bent portion of the element having a first curvature and an ejection portion of the element between the bent portion and the second end of the strip of metal; and bending the strip of metal in a second direction opposite the first direction at the second end of the strip of metal to form a free end of the ejection portion, the free end having a second curvature.

30. The method of clause 29, wherein the bending of the strip of metal in the first direction includes bending the strip of metal such that the second end is rotated about a fulcrum by more than 90 degrees to orient the ejection portion at an acute angle relative to the retention portion.

31. The method of clause 29 or 30, wherein the metal includes steel.

32. The method of any one of clauses 29 to 31, wherein the hole is a first hole, and wherein the defining includes: machining the first hole in the strip of metal on the first side of the strip of metal; and machining a second hole in the strip of metal on the second side of the strip of metal.

33. A spring configured to be disposed within a battery receptacle of a medical device, the spring including: a retention portion to be positioned at a side wall of the battery receptacle, the retention portion configured to deflect and to apply a retention force to a side surface of a battery when the battery is inserted into the battery receptacle; and an ejection portion that terminates in a free end to be positioned a distance from the side wall of the battery receptacle, the free end configured to deflect and to apply an ejection force to an end surface of the battery when the battery is inserted into the battery receptacle.

34. The spring of clause 33, wherein a portion of the retention force is directed orthogonally to a portion of the ejection force.

35. The spring of clause 33 or 34, further including a bent portion interposed between the retention portion and the ejection portion, wherein the retention portion: has a curvature; and is further configured to deflect away from the side wall of the battery receptacle in response to the end surface of the battery pressing the free end.

36. The spring of any one of clauses 33 to 35, wherein the ejection portion is oriented at an acute angle relative to the retention portion.

37. The spring of clause 33 or 34, further including a mounting portion configured to mount the spring to the side wall of the battery receptacle, wherein the retention portion includes a pair of flat springs, each flat spring of the pair of flat springs extending at an angle from the mounting portion at the side wall of the battery receptacle and terminating at an additional free end.

38. The spring of any one of clauses 33 to 37, wherein: the retention portion is biased to return to a first initial position while deflected; and the free end is biased to return to a second initial position while deflected.

39. A power source retention and ejection element for retaining a battery in a receptacle of a medical device, including: an ejection portion; and a retention portion coupled to the ejection portion by a bent portion, wherein engagement of the ejection portion by a battery causes the rotation of the bent portion, the rotation of the bent portion causing the retention portion to deflect and contact a first surface of the battery, the contact substantially restraining movement of the portion of the battery in first direction and the engagement of the battery with the ejection portion causing the ejection portion to exert an ejection force on the battery in a second direction.

40. The power source retention and ejection element of clause 39, wherein the retention portion and the ejection portion describe a first angle there between prior to engagement of the ejection portion by the battery.

41. The power source retention and ejection element of clause 40, wherein the first angle is an acute angle.

42. The power source retention and ejection element of clause 40 or 41, wherein the engagement of the ejection portion by the battery causes the retention and ejection portion to describe a second angle there between and wherein the second angle is larger than the first angle.

43. A retention and ejection spring for a power source of a portable defibrillator, including: a retention portion that, when engaged, applies a retention force against a lateral surface of a power source; and an ejection portion that, from a engaged state, applies an ejection force against an end surface of the power source.

44. The spring of clause 43, wherein at least a portion of the retention force is oriented substantially orthogonally to at least a portion of the ejection force.

45. The spring of clause 43 or 44, wherein the retention portion is deflected and contacts the lateral surface of the power source when the retention portion is engaged.

46. The spring of any one of clauses 43 to 45, wherein the ejection portion includes a free end that contacts the end surface of the power source when the ejection portion is in the engaged state.

47. A retention and ejection spring for a power source of a portable defibrillator, including: a retention portion movable from an initial position to an engaged position; and an ejection portion integrated to the retention portion, the ejection portion movable from an initial position to an engage position, wherein the retention portion is moved to the engaged position in response to the ejection portion being moved to the engaged position.

48. The spring of clause 47, wherein the retention portion and the ejection portion are each biased to return from the engaged positions to the initial positions.

49. A portable medical device, including: a battery receptacle; a battery configured to be inserted into the battery receptacle; and a battery retention and ejection element positioned within the battery receptacle and configured to exert a retention force on the battery in a first direction and an ejection force on the battery in a second direction when the battery is inserted into the receptacle and engages the battery retention and ejection element.

50. The device of clause 49, wherein battery retention and ejection element is a singular element that has a retention portion joined to an ejection portion by a bent portion.

51. The device of clause 50, wherein the retention portion deflects from an initial state to an engaged state when the battery engages the battery retention and ejection element, the deflection of the retention portion causing the retention force on the battery.

52. The device of clause 50 or 51, wherein a free end of the ejection portion is displaced from an initial position to an engaged position when the battery engages the battery retention and ejection element, the displacement of the free end causing the ejection portion to exert the ejection force on the battery.

53. The device of any one of clauses 50 to 52, wherein a displacement of the ejection portion causes a deflection of the retention portion of the battery retention and ejection element.

54. A portable defibrillator including: a battery receptacle configured to receive a battery; and an element positioned within the battery receptacle, wherein the element is a monolithic structure and includes: a retention having a curvature and portion positioned at a side wall of the battery receptacle and configured to contact, and exert a retention force on, a side surface of the battery when the battery is inserted into the battery receptacle; an ejection portion that terminates in a free end positioned a distance from the side wall, wherein the free end of the ejection portion has a rolled lip and is configured to contact, and exert an ejection force on, an end surface of the battery when the battery is inserted into the battery receptacle; a bent portion interposed between the retention portion and the ejection portion, the bent portion causing the ejection portion to be oriented at an acute angle relative to the retention portion prior to insertion of the battery into the battery receptacle; and a mounting portion configured to mount the element to the side wall of the battery receptacle via a hole defined in the mounting portion, wherein the retention portion is interposed between the mounting portion and the bent portion.

55. The portable defibrillator of clause 1, wherein: a concave surface of the bent portion faces the battery when the battery is inserted into the battery receptacle; and a convex surface of the retention portion faces the battery when the battery is inserted into the battery receptacle.

56. A portable defibrillator including: a battery receptacle configured to receive a battery; and an element positioned within the battery receptacle, wherein the element is a monolithic structure and includes: a retention portion positioned at a side wall of the battery receptacle and configured to contact, and exert a retention force on, a side surface of the battery when the battery is inserted into the battery receptacle; and an ejection portion that terminates in a free end positioned a distance from the side wall, the free end of the ejection portion configured to contact, and exert an ejection force on, an end surface of the battery when the battery is inserted into the battery receptacle.

57. An element configured to be disposed within a battery receptacle of a portable defibrillator, wherein the element is a monolithic structure and includes: a retention portion to be positioned at a side wall of the battery receptacle, the retention portion configured to contact the battery and to exert a retention force on a side surface of the battery in a first direction when the battery is inserted into the battery receptacle; and an ejection portion that terminates in a free end to be positioned a distance from the side wall of the battery receptacle, the free end of the ejection portion configured to contact the battery and to exert an ejection force on an end surface of the battery in a second direction different than the first direction when the battery is inserted into the battery receptacle.

58. A method of forming an element to be disposed within a battery receptacle of a portable defibrillator, the method including: defining a hole in a strip of metal at a first end of the strip of metal; bending the strip of metal in a first direction at a first location between the first end of the strip of metal and a second end of the strip of metal to form a bent portion of the element having a first curvature and an ejection portion of the element between the bent portion and the second end of the strip of metal; bending the strip of metal in a second direction opposite the first direction at the second end of the strip of metal to form a free end of the ejection portion, the free end having a second curvature; and bending the strip of metal in the second direction at a second location between the bent portion and the first end of the strip of metal to form a retention portion of the element having a third curvature.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the disclosed techniques and systems in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

The invention claimed is:

1. A portable defibrillator comprising:
a battery receptacle configured to receive a battery; and
an element positioned within the battery receptacle, wherein the element is a monolithic structure and comprises:
a retention portion having a curvature and positioned at a side wall of the battery receptacle and configured to contact, and exert a retention force on, a side surface of the battery when the battery is inserted into the battery receptacle;
an ejection portion that terminates in a free end positioned a distance from the side wall, wherein the free end of the ejection portion has a rolled lip and is configured to contact, and exert an ejection force on, an end surface of the battery when the battery is inserted into the battery receptacle;
a bent portion interposed between the retention portion and the ejection portion, the bent portion causing the ejection portion to be oriented at an acute angle relative to the retention portion prior to insertion of the battery into the battery receptacle; and
a mounting portion configured to mount the element to the side wall of the battery receptacle via a hole defined in the mounting portion, wherein the retention portion is interposed between the mounting portion and the bent portion.

2. The portable defibrillator of claim 1, wherein:
a concave surface of the bent portion faces the battery when the battery is inserted into the battery receptacle; and
a convex surface of the retention portion faces the battery when the battery is inserted into the battery receptacle.

3. The portable defibrillator of claim 1, wherein:
the free end of the ejection portion is movable; and
the ejection portion is configured to be oriented at a second angle relative to the retention portion when the battery is inserted into the battery receptacle, the second angle greater than the acute angle.

4. The portable defibrillator of claim 1, wherein the monolithic structure is made of spring steel.

5. The portable defibrillator of claim 1, wherein the retention portion is configured to deflect away from the side wall of the battery receptacle in response to a deflection of the free end of the ejection portion when the battery is inserted into the battery receptacle.

6. The portable defibrillator of claim 1, wherein the retention portion and the ejection portion are each:
configured to deflect from an initial position when the battery is inserted into the battery receptacle; and
biased to return to the initial position when the battery is removed from the battery receptacle.

7. An element configured to be disposed within a battery receptacle of a portable defibrillator, wherein the element is a monolithic structure and comprises:
a retention portion to be positioned at a side wall of the battery receptacle, the retention portion configured to contact a battery and to exert a retention force on a side surface of the battery in a first direction when the battery is inserted into the battery receptacle; and
an ejection portion oriented at an acute angle relative to the retention portion, wherein the ejection portion terminates in a free end to be positioned a distance from the side wall of the battery receptacle, the free end of the ejection portion configured to contact the battery and to exert an ejection force on an end surface of the battery in a second direction different than the first direction when the battery is inserted into the battery receptacle.

8. The element of claim 7, further comprising a bent portion interposed between the retention portion and the ejection portion, wherein the bent portion causes the ejection portion to be oriented at the acute angle relative to the retention portion.

9. The element of claim 7, wherein:
the free end of the ejection portion is movable; and
the ejection portion is configured to be oriented at a second angle relative to the retention portion when the battery is inserted into the battery receptacle, the second angle greater than the acute angle.

10. The element of claim 8, further comprising a mounting portion configured to mount the element within the battery receptacle, wherein the retention portion is interposed between the mounting portion and the bent portion.

11. The element of claim 7, wherein the retention portion:
has a curvature; and
is configured to deflect away from the side wall of the battery receptacle in response to a deflection of the free end of the ejection portion when the battery is inserted into the battery receptacle.

12. The element of claim 7, wherein the monolithic structure is made of spring steel.

13. The element of claim 7, wherein the free end of the ejection portion has a rolled lip.

14. The element of claim 7, further comprising a mounting portion configured to mount the element within the battery receptacle, wherein the retention portion comprises a pair of flat springs, each flat spring of the pair of flat springs extending at an angle from the mounting portion at the side wall of the battery receptacle and terminating at an additional free end.

15. The element of claim 7, wherein the retention portion and the ejection portion are each:
configured to deflect from an initial position when the battery is inserted into the battery receptacle; and
biased to return to the initial position when the battery is removed from the battery receptacle.

16. The element of claim 10, wherein the mounting portion is configured to mount the element to the side wall of the battery receptacle via a hole defined in the mounting portion.

17. The element of claim 16, wherein the hole is configured to receive a fastener to mount the element to the side wall of the battery receptacle.

18. The element of claim 8, wherein:
a concave surface of the bent portion faces the battery when the battery is inserted into the battery receptacle;
the retention portion has a curvature; and
a convex surface of the retention portion faces the battery when the battery is inserted into the battery receptacle.

19. The element of claim 10, wherein the retention portion tapers lengthwise along the element from the mounting portion to the bent portion.

20. The element of claim 8, wherein the bent portion includes an opening defined in a center of the bent portion.

* * * * *